US008545476B2

(12) United States Patent
Ariagno et al.

(10) Patent No.: US 8,545,476 B2
(45) Date of Patent: Oct. 1, 2013

(54) ASSEMBLY TO FACILITATE USER RECONSTITUTION

(75) Inventors: Scott R. Ariagno, Palatine, IL (US); Frederick Charles Houghton, II, Moorpark, CA (US); Daniel E. Roush, Niles, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 102 days.

(21) Appl. No.: 13/217,967

(22) Filed: Aug. 25, 2011

(65) Prior Publication Data

US 2012/0053555 A1 Mar. 1, 2012

Related U.S. Application Data

(60) Provisional application No. 61/376,912, filed on Aug. 25, 2010.

(51) Int. Cl.
*A61B 19/00* (2006.01)

(52) U.S. Cl.
USPC ........... 604/414; 604/411; 604/412; 604/413; 604/416

(58) Field of Classification Search
USPC .................................................. 604/411–416
See application file for complete search history.

(56) References Cited

U.S. PATENT DOCUMENTS

| | | | |
|---|---|---|---|
| 4,410,321 | A | 10/1983 | Pearson et al. |
| 4,411,662 | A | 10/1983 | Pearson |
| 4,432,755 | A | 2/1984 | Pearson |
| 4,576,211 | A | 3/1986 | Valentini et al. |
| 4,583,971 | A | 4/1986 | Bocquet et al. |
| 4,606,734 | A | 8/1986 | Larkin et al. |
| 4,759,756 | A | 7/1988 | Forman et al. |
| 4,936,841 | A | 6/1990 | Aoki et al. |

(Continued)

FOREIGN PATENT DOCUMENTS

| | | | |
|---|---|---|---|
| DE | 69903266 | T2 | 6/2003 |
| DE | 102006031712 | B3 | 7/2006 |
| EP | 0614653 | A3 | 9/1994 |
| WO | WO2008006439 | A1 | 1/2008 |

OTHER PUBLICATIONS

International Preliminary Report on Patentability for International Application No. PCT/USD2011/0491135 dated Sep. 4, 2012.

(Continued)

*Primary Examiner* — Leslie Deak
(74) *Attorney, Agent, or Firm* — K&L Gates LLP

(57) ABSTRACT

A reconstitution assembly includes a housing including a lower sleeve and an upper sleeve, including a first container and a second container disposed vertically opposite the first container. A transfer set assembly is disposed within the housing between the first container and the second container. The transfer set assembly includes an upper spike housing and a lower spike housing, with a flow path defined through the upper spike housing and the lower spike housing. The transfer set assembly is configured to access contents of the first container and then upon the activation of a triggering mechanism, create a fluid pathway between the first container and the second container. The triggering mechanism includes trigger fingers which ensure the transfer set assembly sequentially accesses the contents of the first container before accessing the contents of the second container. The disposition of the first container activates the triggering mechanism.

23 Claims, 14 Drawing Sheets

(56) References Cited

U.S. PATENT DOCUMENTS

| | | | |
|---|---|---|---|
| 5,116,316 | A | 5/1992 | Sertic et al. |
| 5,308,347 | A | 5/1994 | Sunago et al. |
| 5,342,346 | A | 8/1994 | Honda et al. |
| 5,352,191 | A | 10/1994 | Sunago et al. |
| 5,364,386 | A | 11/1994 | Fukuoka et al. |
| 5,445,631 | A | 8/1995 | Uchida |
| 5,478,337 | A | 12/1995 | Okamoto et al. |
| 5,779,668 | A | 7/1998 | Grabenkort |
| 5,826,713 | A | 10/1998 | Sunago et al. |
| 6,022,339 | A | 2/2000 | Fowles et al. |
| 6,070,623 | A | 6/2000 | Aneas |
| 6,113,583 | A | 9/2000 | Fowles et al. |
| 6,258,078 | B1 | 7/2001 | Thilly |
| 6,558,365 | B2 | 5/2003 | Zinger et al. |
| 6,571,837 | B2 | 6/2003 | Jansen et al. |
| 6,582,415 | B1 | 6/2003 | Fowles et al. |
| 6,645,171 | B1 | 11/2003 | Robinson et al. |
| 6,852,103 | B2 | 2/2005 | Fowles et al. |
| 6,890,328 | B2 | 5/2005 | Fowles et al. |
| 6,915,823 | B2 | 7/2005 | Osborne et al. |
| 6,948,522 | B2 | 9/2005 | Newbrough et al. |
| 7,358,505 | B2 | 4/2008 | Woodworth et al. |
| 7,425,209 | B2 | 9/2008 | Fowles et al. |
| 7,491,197 | B2 * | 2/2009 | Jansen et al. .................. 604/413 |
| 7,540,863 | B2 | 6/2009 | Haindl |
| 7,753,085 | B2 | 7/2010 | Tribble et al. |
| 8,100,154 | B2 | 1/2012 | Reynolds et al. |
| 2001/0003996 | A1 | 6/2001 | Jansen et al. |
| 2002/0087141 | A1 | 7/2002 | Zinger et al. |
| 2002/0123736 | A1 | 9/2002 | Fowles et al. |
| 2003/0036725 | A1 | 2/2003 | Lavi et al. |
| 2003/0199846 | A1 | 10/2003 | Fowles et al. |
| 2004/0045567 | A1 | 3/2004 | Lewis et al. |
| 2004/0059312 | A1 | 3/2004 | Frezza et al. |
| 2004/0154690 | A1 | 8/2004 | Osborne et al. |
| 2004/0199139 | A1 | 10/2004 | Fowles et al. |
| 2004/0241041 | A1 | 12/2004 | Woodworth et al. |
| 2004/0249341 | A1 | 12/2004 | Newbrough et al. |
| 2005/0133729 | A1 | 6/2005 | Woodworth et al. |
| 2005/0137566 | A1 | 6/2005 | Fowles et al. |
| 2007/0088315 | A1 | 4/2007 | Haindl |
| 2007/0125442 | A1 | 6/2007 | Tribble et al. |
| 2008/0172001 | A1 | 7/2008 | Reynolds et al. |
| 2008/0188799 | A1 | 8/2008 | Mueller-Beckhaus et al. |
| 2008/0300570 | A1 | 12/2008 | Fowles et al. |
| 2009/0182300 | A1 | 7/2009 | Radmer et al. |
| 2009/0318893 | A1 | 12/2009 | English |
| 2010/0004618 | A1 | 1/2010 | Rondeau et al. |
| 2010/0106129 | A1 | 4/2010 | Goeckner et al. |
| 2010/0161113 | A1 | 6/2010 | Tribble et al. |
| 2010/0168712 | A1 | 7/2010 | Tuckwell et al. |
| 2010/0191182 | A1 | 7/2010 | Smith et al. |
| 2010/0217431 | A1 | 8/2010 | Tribble et al. |

OTHER PUBLICATIONS

International Search Report and Written Opinion for International Application No. PCT/US2011/049135 dated Dec. 13, 2011.

* cited by examiner

ASSEMBLY TO FACILITATE USER RECONSTITUTION

PRIORITY CLAIM

This application claims priority to and the benefit of U.S. Provisional Patent Application No. 61/376,912, filed on Aug. 25, 2010, the entire contents of which is incorporated by reference herein.

BACKGROUND

The present disclosure relates generally to a reconstitution assembly. More specifically, the present disclosure relates to a drug reconstitution assembly for reconstituting a lyophilized drug.

Certain drugs are supplied in lyophilized form. The lyophilized drug must be mixed with water to reconstitute the drug into a form suitable for injection into a patient. In particular, all of the components that contact the drugs must be sterile to avoid the chance of infection.

The reconstitution process presents difficulties for many people which are in need of injecting themselves or another family member in a home environment. The general process requires the exact, sequential manipulation of the drug vial, the diluent container and the transfer syringes which must utilize needles to penetrate the vial stoppers. This process should be done with good aseptic practices.

In addition, many lyophilized drugs are provided in vials having the interior at a negative pressure relative to the atmosphere. This negative pressure facilitates reconstitution as it compensates for the volume of diluents which is injected into the vial for reconstitution. If air is allowed to enter into the interior of the vial prior to the injection of the diluents, this may make the reconstitution process much more difficult for the patient or health care provider.

Thus, reconstitution presents challenges in ensuring sterility of the product and providing ease of use to the patient or caregiver. The lyophilized drugs are often very expensive, making the minimization of the mechanical and user error of the utmost importance to avoid product waste. In particular, it is desirable to maintain user interaction with the reconstitution assembly to a minimum and to minimize the number of steps in the reconstitution process. In addition it is desirable to prevent unintentional or intentional tampering with the diluent or drug container and reuse of the reconstitution assembly. Moreover, it is desirable to minimize or eliminate the ability of the user to negatively impact the reconstitution process during user interaction.

SUMMARY

The present disclosure provides a reconstitution assembly that is especially useful for reconstituting a lyophilized drug for use by a patient.

In one embodiment, a reconstitution assembly includes a housing including an upper sleeve and lower sleeve. The housing defines a generally tubular passageway and has an outer surface defining a user friendly configuration. A transfer set assembly is disposed within the housing between the lower sleeve and the upper sleeve. The transfer set assembly includes a pair of opposing spikes forming a portion of a fluid flow path having upper and lower ends.

A first container, typically including a diluent, is disposed inside the upper sleeve, within the passageway and adjacent the upper end of the flow path. The first container includes a first seal cap providing a sterile barrier to contents of the first container. The first container is disposed with the first seal cap facing downward. A second container is disposed inside the lower sleeve within the passageway and adjacent the lower end of the flow path. The second container includes a second seal cap providing a sterile barrier to the contents of the second container. In an embodiment, the contents of the second container contains are sealed by the second seal cap under a vacuum. The second container is disposed with the second seal cap facing upward toward the first seal cap. The upper sleeve is configured to engage the first container to prevent removal of the first container from the assembly.

A triggering mechanism sits adjacent to and is engaged to the second container and disposed within the lower sleeve of the housing and within the passageway. The triggering mechanism is situated within the housing to place the second container in a resting position and prevent the movement of the second container relative to the transfer set assembly until fluid communication is established between the interior of the first container and the upper end of the flow path. The trigger mechanism is also configured to prevent removal of the second container from the assembly.

In an embodiment, the spike at the upper end of the flow path pierces the first seal cap upon application of a first predetermined force to the first container. The first predetermined force may be applied to the end of the first container opposite the first seal cap. The force may be applied by the user grasping the housing in a vertical orientation, contacting the lower end of the second container against a surface and pushing the first container downward. Subsequent to the spike at the upper end of the flow path piercing the first seal cap of the first container, the periphery of a rim of the first container, which accepts the first seal cap, is configured to engage the triggering mechanism.

The engaged triggering mechanism is configured to allow the second container to then move axially relative to the transfer set assembly. The spike at the lower end of the flow path pierces the second seal cap upon application of a second predetermined force and the engagement of the triggering mechanism by the first container. When the second seal cap is pierced, the vacuum of the second container is accessed. The second predetermined force may be applied by maintaining the contact between the bottom of the second vial and the surface and continuing to apply a downward force to the first container.

In an embodiment, the first container encloses a liquid and the second container encloses a lyophilized product. Once the first cap of the first container is pierced with the spike at the upper end of the flow path and the second seal cap of the second container is thereafter pierced with the spike at the lower end of the flow path, the first and second containers are in fluid communication through the flow path of the transfer set assembly. Due to the vacuum of the second container, the liquid of the first container is aspirated through the fluid pathway into the second container after the first and second containers are placed into fluid communication with one another.

Thus the liquid from the first container is drawn into the second container to allow mixture with the medication in that container and requires no complicated interaction by the user other than placing the assembly in a vertical orientation on a surface and then pushing on the top of the assembly. The reconstitution assembly may then be gently agitated to mix the lyophilized product of the second container with the liquid from the first container to form a reconstituted product.

The transfer set assembly housing includes a port and forms an access path to provide fluid communication between the port and a portion of the second spike that is exposed to the interior of the second container when the second spike pierces the second seal cap. The port is disposed on the transfer set housing and extends substantially perpendicular to the flow path through the housing to the exterior of the housing. In one embodiment, the port is separated from the access path with a valve or a port seal. After the reconstituted product is formed, a patient or caregiver accesses the liquid through the port by opening the valve or removing the port seal and withdrawing the reconstituted product through the access path into a syringe without the use of a needle.

Additional features and advantages are described herein, and will be apparent from the following Detailed Description and the figures.

DETAILED DESCRIPTION

The present disclosure provides reconstitution assemblies that are especially useful for reconstituting a lyophilized drug. Although the assemblies are described primarily herein with respect to reconstituting a lyophilized drug, it will be apparent that the assemblies may be used to reconstitute other materials as well.

Figure 1:
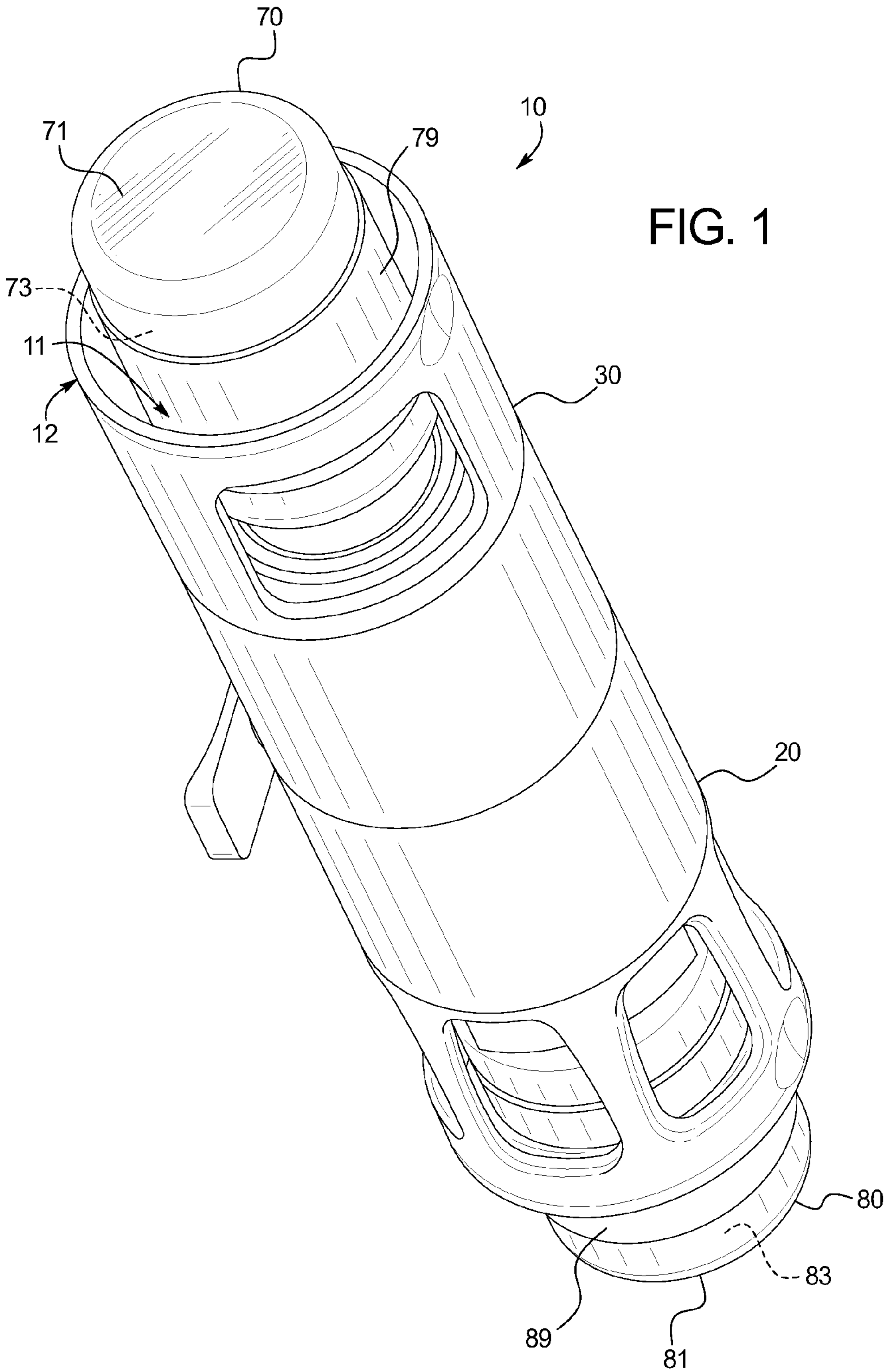
FIG. 1 is a perspective view of one embodiment of a reconstitution assembly.
Figure 2:
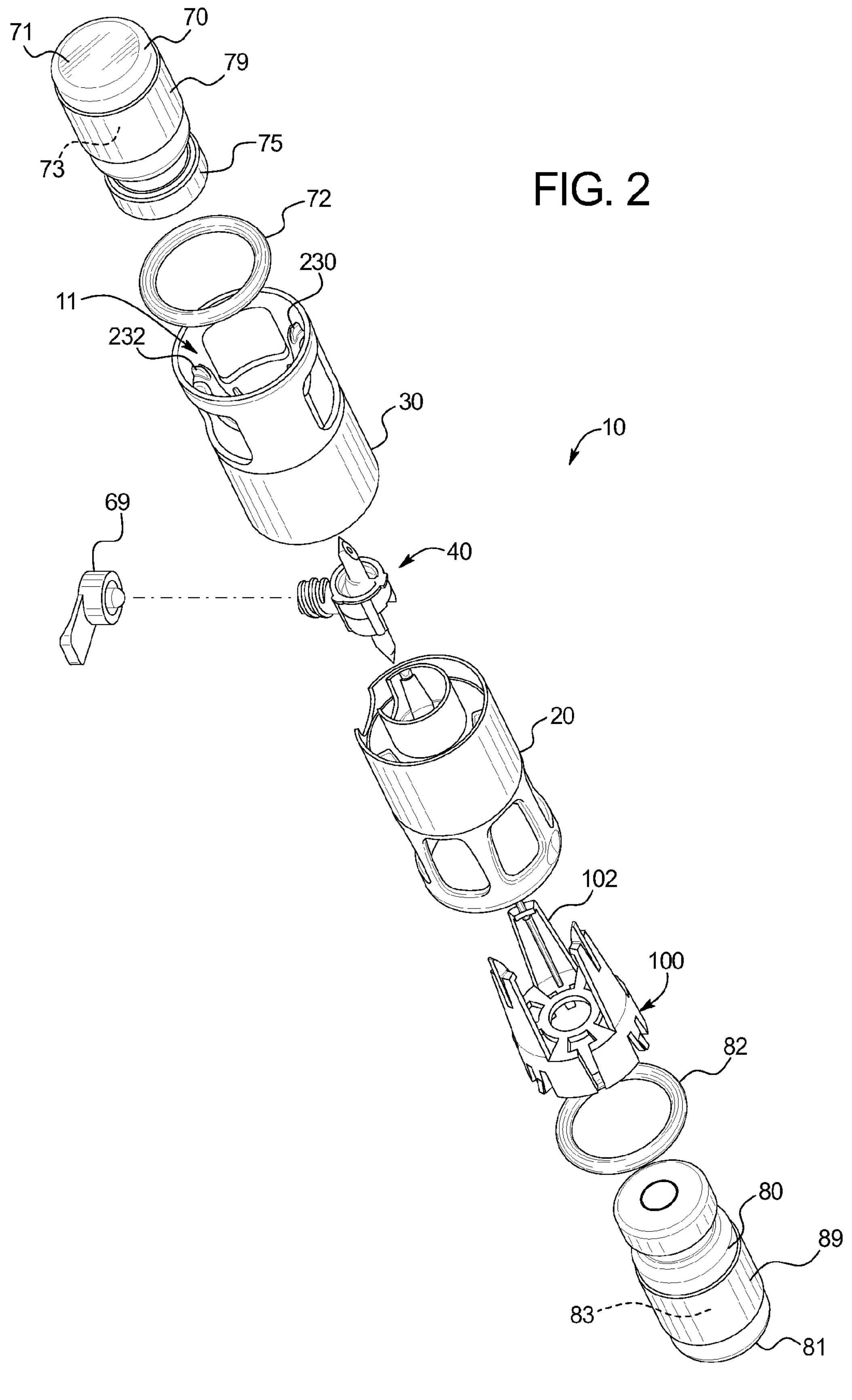
FIG. 2 is an exploded view of the reconstitution assembly of FIG. 1 showing one embodiment of a triggering mechanism of the present disclosure.

Referring now to the drawings and in particular to FIGS. 1 and 2, a reconstitution assembly 10 is shown. Assembly 10 includes a housing 12. The housing 12 maintains alignment and constrains motion of the internal components. The housing 12 includes a first or lower sleeve 20 and a second or upper sleeve 30 and defines a generally cylindrical internal passageway 11. At least a portion of the first container 70 is disposed in second or upper sleeve 30 and passageway 11 and at least a portion of a second container 80 is disposed in first or lower sleeve 20 and passageway 11. The housing 12 may be surrounded by packaging during storage and shipping.

A transfer set assembly 40 (FIG. 2) is disposed within the housing 12, fixed between containers 70 and 80. The transfer set assembly 40 is lockingly engaged with and fixed relative to the first sleeve 20 and second sleeve 30. Upon activation of the assembly 10, the transfer set assembly 40 provides a mechanism for transferring the contents of the first container 70 located in second sleeve 30 into the second container 80 located in bottom sleeve 20 of the assembly 10 in an efficient and sterile manner and also to provide a reconstituted drug for a user.

Sleeves 20 and 30 are made of a suitable moldable and sterilizable plastic such as ABS, PC or acrylic. The containers 70, 80 may be made of any suitable medical grade material for holding a substance, such as glass or plastic, and an elastomeric stopper. In one embodiment, container 70 contains sterilized water and container 80 contains a lyophilized drug. Assembly 10 provides a two-stage reconstitution method for adding the water 73 to the lyophilized drug 81 to reconstitute the drug and withdrawal of the reconstituted drug into a syringe. Assembly 10 provides a sterile mechanism for accomplishing the reconstitution goal, minimizes the chance of user mistakes and reduces the possibility of wasting lyophilized drug 81.

It should be appreciated that each of sleeves 20 and 30 include a plurality of windows spaced radially around the sleeves 20, 30. It should be appreciated that, by including a plurality of windows, the sterilization of internal parts and components is made easier. As discussed in more detail below, in various embodiments, the various components are sterilized with hydrogen peroxide vapor although other gaseous sterilants such as ethylene oxide are also contemplated.

Figure 3:
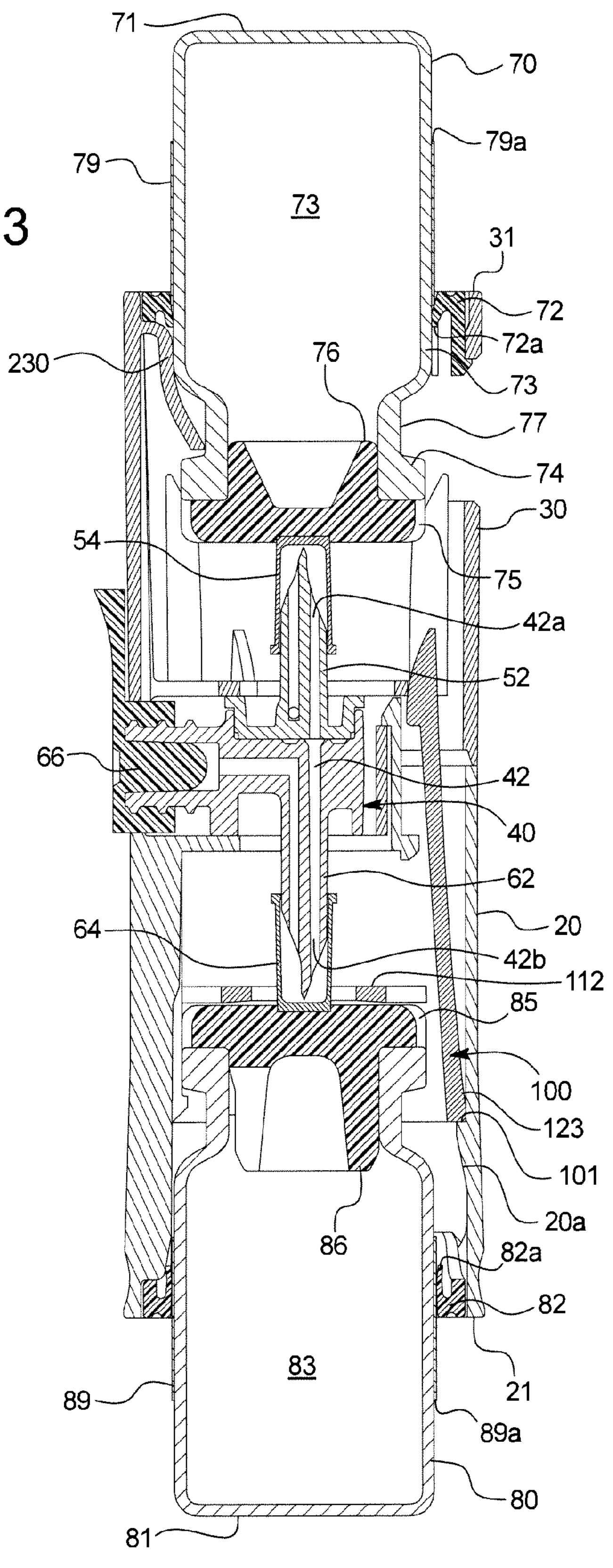
FIG. 3 is a sectioned elevational view of the reconstitution assembly of FIG. 1 in a first configuration.
Figure 8:
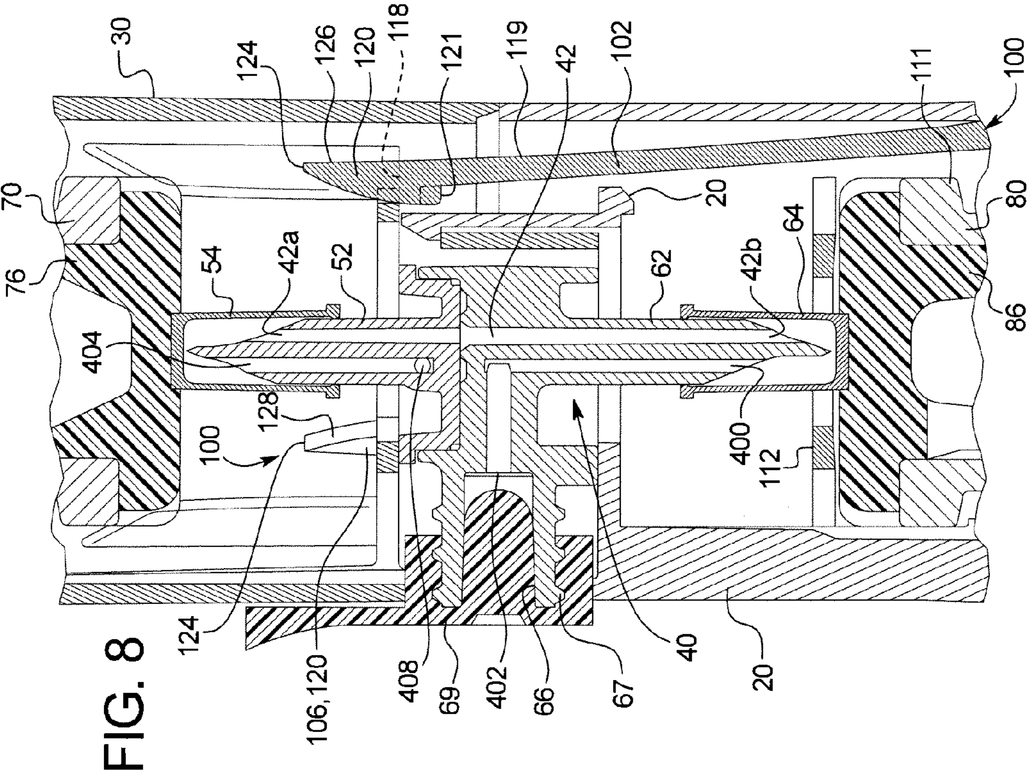
FIG. 8 is a sectioned elevational view of the triggering mechanism of FIG. 1 showing a first stage in the use of the reconstitution assembly.

Referring additionally to FIG. 3, the transfer set assembly 40 includes an upper spike housing and a lower spike housing. An upper spike 52 forms a portion of and is preferably integrated into the upper spike housing. A lower spike 62 forms a portion of and is preferably integrated into the lower spike housing. Each of the lower spike 62 and upper spike 52 defines a flow path 42 to pass through the spikes. Spike housing, upper spike 52 and lower spike 62 can be made of a polymeric material. The transfer set assembly 40 also includes an upper boot 54 which fits over at least a portion of the upper spike 52 and the upper end **42*a* of the flow path 42, and a lower boot 64 which fits over at least a portion of the lower spike 62 and the lower end 42*b* of the flow path 42 (as seen in FIG. 8). In one embodiment, the upper boot 54 and lower boot 64 are made of an elastomeric material to ensure sterility of the flow path 42. The lower boot 64 also provides a barrier to leakage of fluid from the flow path 42 onto the container 80. It should be appreciated that the boots 54 and 64 extend from the tip of the upper and lower spikes 52 and 62 respectively, toward the base of the spikes of the transfer set assembly 40. In various embodiments, the boots 54, 64 do not extend entirely from the tip of each of the spikes 52, 62 to the base of the spikes, but extend only partially along the spike exposing a portion of the spike to the environment. It should be appreciated that, as discussed further below, the smaller boots 54, 64 result in less elastomeric material which is to be pushed aside upon activation of the reconstitution device. By using less material, the interference is minimized, but the flow paths are still protected from the outside environment and will maintain sterility after removal of the assembly 10 from packaging. In an embodiment, the lengths of spikes 52 and 62 are reduced slightly, to avoid any contact between boots 54 and 64 with vials 70 and 80** prior to activation. Maintaining a gap between boot and vial facilitates sterilization.

As seen in FIGS. 1 to 3, first container 70 is disposed adjacent upper boot 54 and the upper end of the spike 52, and is disposed at least partially within the portion of the passageway 11 formed by second sleeve 30. An upper surface 71 of the container 70 is disposed above an upper rim 31 of the second sleeve at a distance selected to provide for movement of the container 70 relative to the sleeve 30 sufficient to provide for engagement of the container with the upper spike 52 as described below, while still keeping the upper surface 71 level or slightly above the rim 31.

First container 70 is held in place in part by the wall of the second sleeve 30. An elastomeric gasket 72 or in a further embodiment, a semi-rigid thermoplastic washer (not shown) fits between first container 70 and upper sleeve 30. The first container 70 includes a seal cap 76, which may be a standard rubber vial stopper. Seal cap 76 is pierceable by the end or tip of upper spike 52. In a further embodiment, gasket 72 is formed as an elastomeric o-ring, which provides frictional contact between first container 70 and upper sleeve 30. In an embodiment, the o-ring or gasket 72 is coated with a lubricating coating to allow the first container 70 to move relative to upper sleeve 30 with reduced friction resistance. The gasket 72 provides optimal and consistent friction resistance across a broad range of vial diameters, which typically vary within a 1 mm range.

A second container 80 is disposed near lower boot 64 and the lower end of spike 62, and at least partially within the portion of the passageway 11 formed by the lower sleeve 20. A lower surface 81 is disposed below a lower rim 21 of the lower sleeve at a distance selected to provide for movement of the container 80 relative to the sleeve 20 sufficient to provide for engagement of the container with the lower spike 62 as described below while still keeping the lower surface 81 level or slightly below the rim 21.

Second container 80 is partially held in place by an elastomeric gasket 82. Second container 80 includes a seal cap 86 which can be a rubber stopper, and is capable of being pierced by the end of lower spike 62. Seal cap 86 provides a seal with container to maintain a vacuum within the container and assist in the reconstitution of the drug as described below. In a further embodiment, gasket 82 is an o-ring, which provides frictional contact between second container 80 and lower sleeve 20. In an embodiment, o-ring or gasket 82 is coated with a lubricating coating to allow second container 80 to move relative to lower sleeve 20 with reduced friction resistance. The gasket 82 provides optimal and consistent friction resistance across a broad range of vial diameters, which typically vary within a 1 mm range.

The reconstitution assembly 10 includes fluid pathways or channels to provide fluid communication from first container 70 to second container 80 and from the second container 80 to a withdrawal port 66 (FIG. 6) of the transfer set assembly 40 that extends generally perpendicular to the orientation of the spikes for access by a user. Withdrawal port 66 is attached to the lower spike housing of the transfer set assembly 40 as seen in FIG. 2. Withdrawal port 66 extends radially outwardly from the lower spike housing, and extends through a portion of the wall of the lower sleeve 20 and upper sleeve 30 of the housing 12. It should be appreciated that in various embodiments, a withdrawal port cap 69 seals the withdrawal port and is constructed from silicon, which is impervious to any degradation caused from a hydrogen peroxide sterilization of the system.

Figure 4:
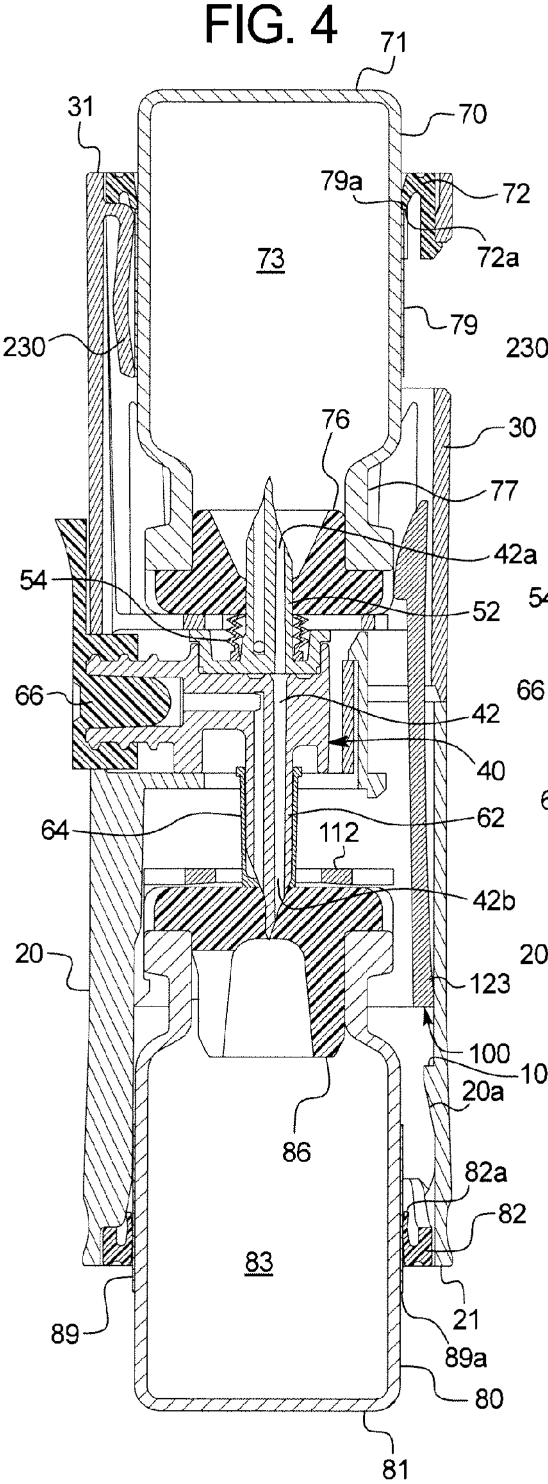
FIG. 4 is a sectioned elevational view of the reconstitution assembly of FIG. 1 in a second configuration.
Figure 5:
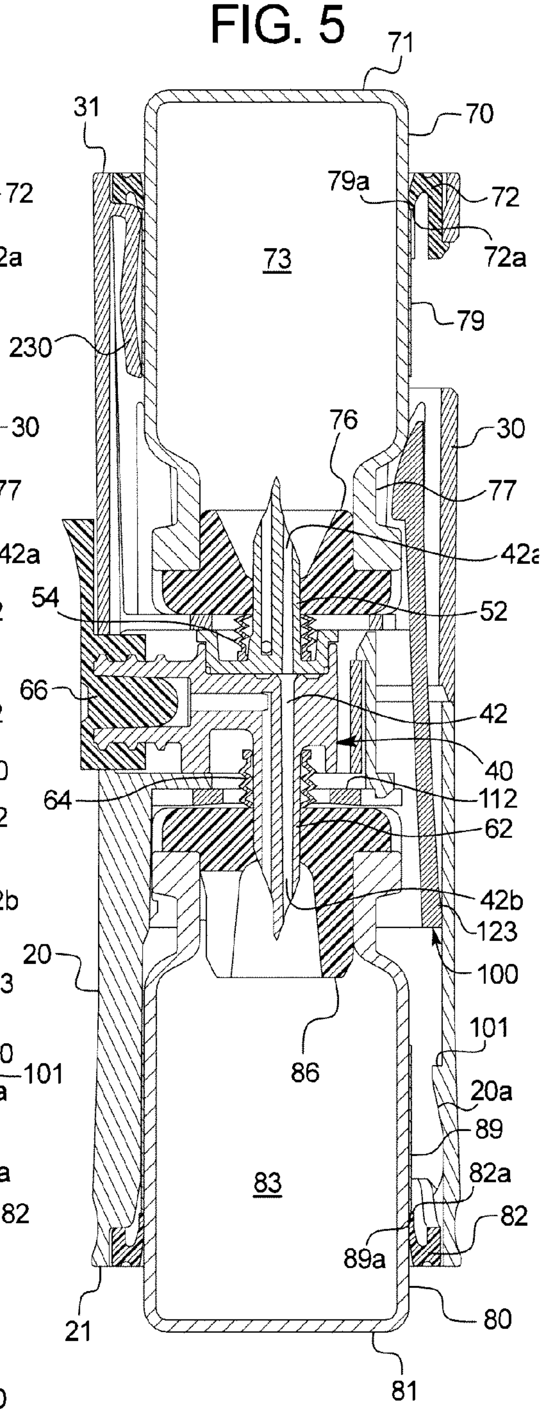
FIG. 5 is a sectioned elevational view of the reconstitution assembly of FIG. 1 in a third configuration.

Referring now to FIGS. 3 to 5, the reconstitution assembly 10 is operable between an initial unactivated or resting configuration (as shown in FIG. 3), a partially activated configuration (as shown in FIG. 4), and a fully activated configuration (as shown in FIG. 5). The first container 70 is movable downwardly or axially relative to and toward the second container 80.

Referring specifically to FIG. 3, in an initial unactivated or resting configuration, seal cap 76 of first container 70 is intact, seal cap 86 of the second container 80 is intact to provide a barrier to the interior of each of the first and second containers 70, 80. Each of the upper boot 54 and lower boot 64 is also intact to maintain the sterility of flow path 42. It should be appreciated that, in the resting or unactivated position, at least a portion of the upper spike 52 has not penetrated the seal cap 76 of the first container 70 or broken the sterile barrier maintained by the upper boot 54. Additionally, in the resting or unactivated position, at least a portion of the lower spike 62 has not penetrated the seal cap 86 of the second container 80 or broken the sterile barrier maintained by the lower boot 64. As seen in FIG. 3, the first container 70 and second container 80 are both positioned in the resting or unactivated state.

Prior to activation the user grips the assembly 10 and places the assembly in a vertically oriented position with the lower surface 81 of the second container 80 resting on a flat surface. Referring specifically to FIG. 4, in partially activated configuration, a manual, pressing force is applied to upper surface 71 of the first container 70 in the downward direction towards the second container 80. The first container 70 moves downward relative to the second sleeve 30 and first sleeve 20. As the upper surface is separated from the rim 31 of the upper sleeve 30, the user can maintain such a manual force isolated on the upper surface without engaging rim 31 during movement of the first container 70. It should be appreciated that, when fluid communication is established between flow path 42 through spike 52 of the transfer set assembly 40 and the interior of the first container 70, the first container 70 is in the activated position.

Transfer set assembly 40 is engaged to and held stationary relative to the second sleeve 30 and first sleeve 20. As first container 70 is moving downward towards second container 80, the seal cap 76 comes into contact with the transfer set assembly 40 at the upper boot 54. The upper spike end of the upper spike 52 of the upper spike housing pierces the upper boot 54 and the seal cap 76 of the first container 70. Once the upper end 42*a* of the flow path 42 formed by the upper spike 52 penetrates through the seal cap 76 of the first container 70, the contents of the first container 70, e.g., sterilized water, are in fluid communication with the flow path 42 and transfer set assembly 40. When the upper spike 52 fully penetrates the seal cap 76 the upper surface 71 of container 70 should be approximately level or extend slightly above the rim 31.

It should be appreciated that in various embodiments, a small amount of a lubricant is applied to the tip of the upper end of spike 52 and the lower end of spike 62 prior to boots 54 and 64 being installed over the spikes. By including a small amount of lubricant on the tip of the spikes, the spikes more easily pass through the caps of the first and second containers

70, 80 with relatively low amount of effort required and with relatively low and consistent deflection of elastomeric vial caps 76 and 86. It should be appreciated that, at the point of this second configuration of FIG. 4, lower boot 64 is still intact, and a seal within withdrawal port 66 (FIG. 6) is still intact.

As discussed in more detail below, when first container 70 is shifted fully downward onto the transfer set assembly 40, and the seal cap 76 has been fully penetrated, the first container engages and activates triggering mechanism 100 shown in more detail in FIGS. 8 to 11. When triggering mechanism 100 becomes activated, second container 80 is enabled to move relative to housing 12 and first container 70 towards the transfer set assembly 40, and more particularly, the lower spike end of the lower spike 62 of the lower spike housing.

Referring now to FIG. 5, in the fully activated configuration, triggering mechanism 100 has been activated, and second container 80 has become free to move relative to the housing 12 towards transfer set assembly 40. Second container 80 moves upwardly relative to the lower sleeve 20 and upper sleeve 30, while seal cap 86 first comes into contact with transfer set assembly 40 at the lower boot 64. As the manual force is continuously applied axially downwardly by the user on the first container, the lower spike end of the lower spike 62 pierces the lower boot 64 and the seal cap 86 of the second container 80. As the lower surface 81 is separated from the rim 21 of the lower sleeve 20, the second container 80 may move relative to the lower sleeve 20 without the lower sleeve engaging the surface on which the assembly 10 has been placed.

At the point when the lower boot 64 and the seal cap 86 are pierced to expose the lower end 42*b* of the flow path 42 to the interior of the second container 80, flow path 42 provides fluid communication between the first container 70 and second container 80 and fluid 73 from first container 70 flows through the flow path 42 and comes into contact with the drug 83 of second container 80.

Figure 6:
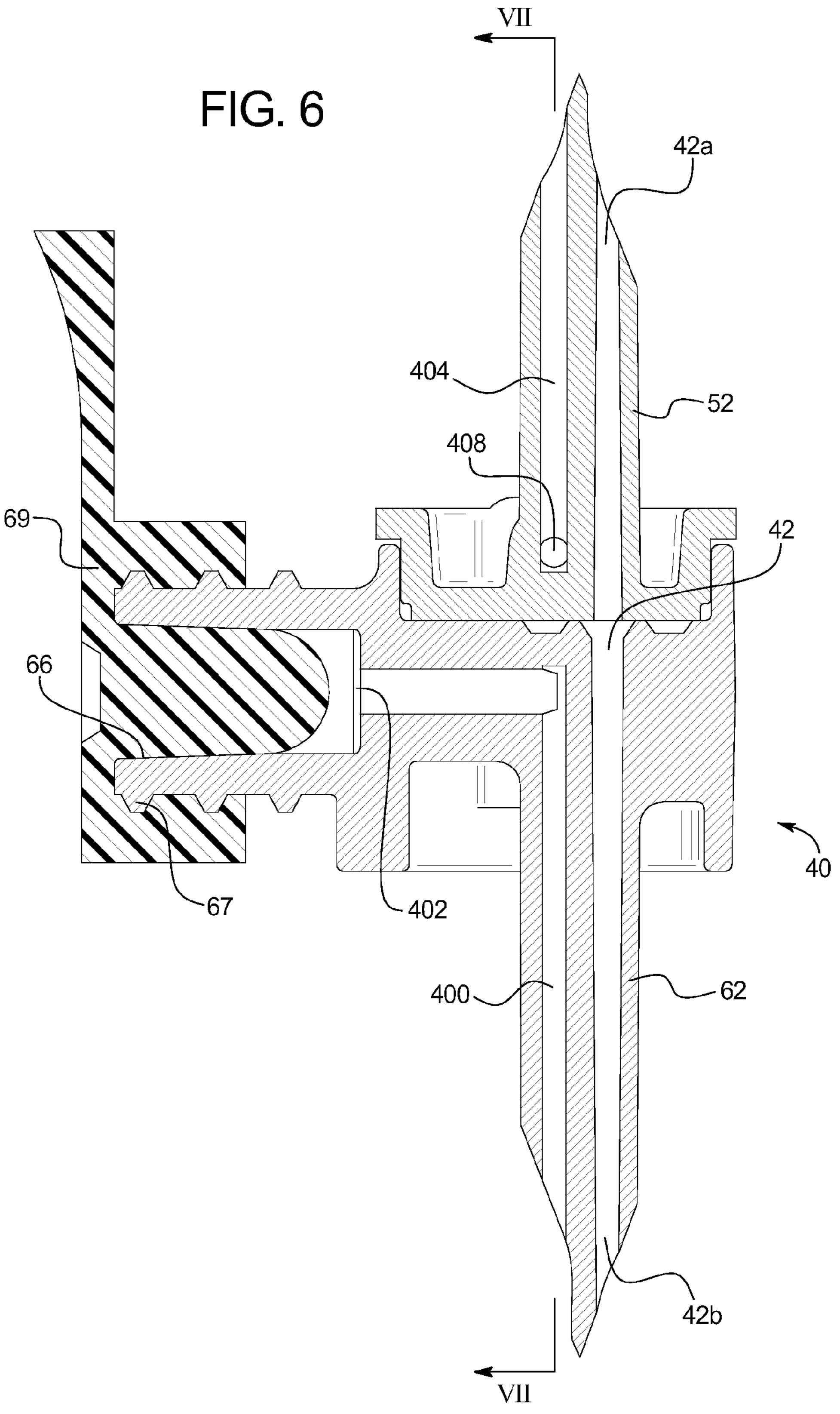
FIG. 6 is a sectioned cutaway view of one embodiment of the transfer set assembly of the present disclosure.
Figure 7:
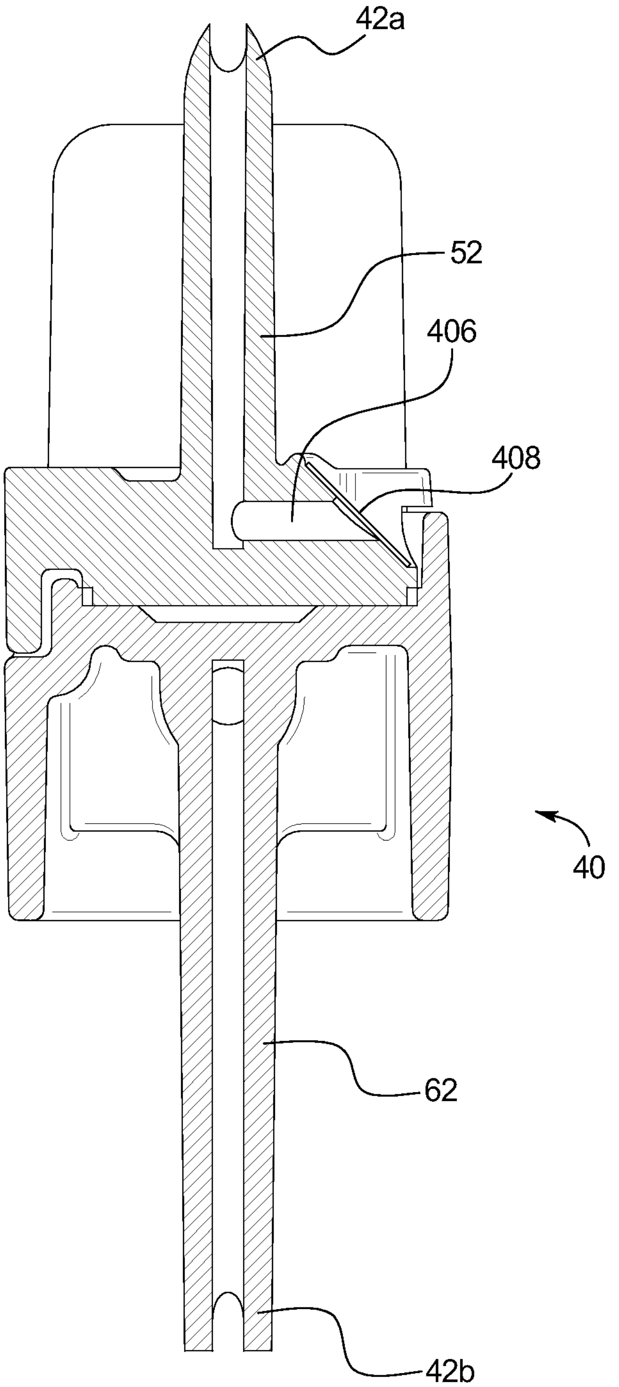
FIG. 7 is a sectional elevation of the transfer set assembly of FIG. 6 taken along line VII-VII of FIG. 6.

Typically, second container 80 is configured to enclose its contents under a vacuum, and therefore, when the second seal cap 86 and the lower boot 64 are penetrated fully, the vacuum in the second container 80 is opened to the contents of first container 70. After the seal cap has been penetrated by the lower spike 62, the negative pressure of the vacuum within the second container 80 causes the contents of the first container 70 to be aspirated through the flowpath 42 defined by transfer set assembly 40 and into the second container 80. During fluid transfer from first container 70 to second container 80, the seal 69 at the withdrawal port 66 prevents ingress of air, which would relieve the vacuum and delay or prevent transfer. Similarly, lower spike 62 creates a seal where it penetrates lower seal cap 86. Atmospheric air is allowed enter the first container 70 through vent path 404 and hydrophobic filter 408, as shown in FIGS. 6 and 7. Venting in this manner prevents negative pressure buildup in the first container 70 and increases the speed of fluid transfer. After the liquid contents of first container 70 are successfully transferred through the fluid pathway of transfer set assembly 40 and into second container 80, the reconstitution assembly 10 is agitated manually to form a reconstituted drug utilizing the liquid contents originally sealed in the first container 70 with the contents originally sealed in the second container 80.

It should be understood that vacuum in the second container may be created or re-created at any time using a syringe connected to the withdrawal port. This allows users to recover from errors that result in vacuum loss without transfer of fluid. Such errors include removal of the withdrawal port seal before activating the device or activating the device upside down.

Referring now to FIGS. 8 to 15, a more detailed view of triggering mechanism 100 is illustrated. Similar to FIGS. 3 to 5, FIGS. 8 to 11 and 14 and 15 illustrate pre-activated or resting, partially activated, and fully activated configurations of the triggering mechanism 100 and thus reconstitution assembly 10, respectfully. Unlike FIGS. 3 to 5, however, FIGS. 8 to 11 display only partial views of the second sleeve 30 and the triggering mechanism 100 in each configuration for ease of illustration and to better illustrate the functionality of the triggering mechanism 100 in cooperation with second sleeve 30.

Triggering mechanism 100 includes a circular base 110, with a radial flange 112 and a wall section 114, which in the illustrated embodiment is substantially frusto-conical in shape. Wall section 114 depends from top flange 112 of the circular base 110 and forms a bottom edge 116 of the circular base 110. Three trigger fingers 102, 104 and 106 (see FIG. 2) are disposed radially around circular base 110, roughly one-hundred twenty degrees apart from one another, and extend upwardly from flange 112. Other numbers and disposition of trigger fingers around the base are also envisioned. In the trigger mechanism's pre-activated state of FIG. 8, the three trigger fingers 102, 104, 106 are formed to tilt slightly radially inwardly.

In one embodiment, the three trigger fingers 102, 104 and 106 include identical features. The features described for trigger finger 106 apply equally for fingers 104 and 102 accordingly. The top of trigger finger 106 includes a shoulder portion 118. Shoulder portion 118 includes shoulders 118*a* and 118*b* and a protruding tapered flange 120, which extends upwardly between shoulder 118*a* and shoulder 118*b*. The surface of shoulder 118 extends radially inwardly from the outer shoulder wall 119 (FIGS. 6 to 12) to inner shoulder wall 122 (correspondingly shown on finger 104). It should be appreciated that the inner shoulder wall 122 of trigger finger 106 and the corresponding inner shoulder walls of each of trigger fingers 102 and 104 are arcuate. The shoulder walls of each of trigger fingers 102, 104 and 106 each strike a common arc and have a common center point with a central axis through triggering mechanism 100.

Figure 12:
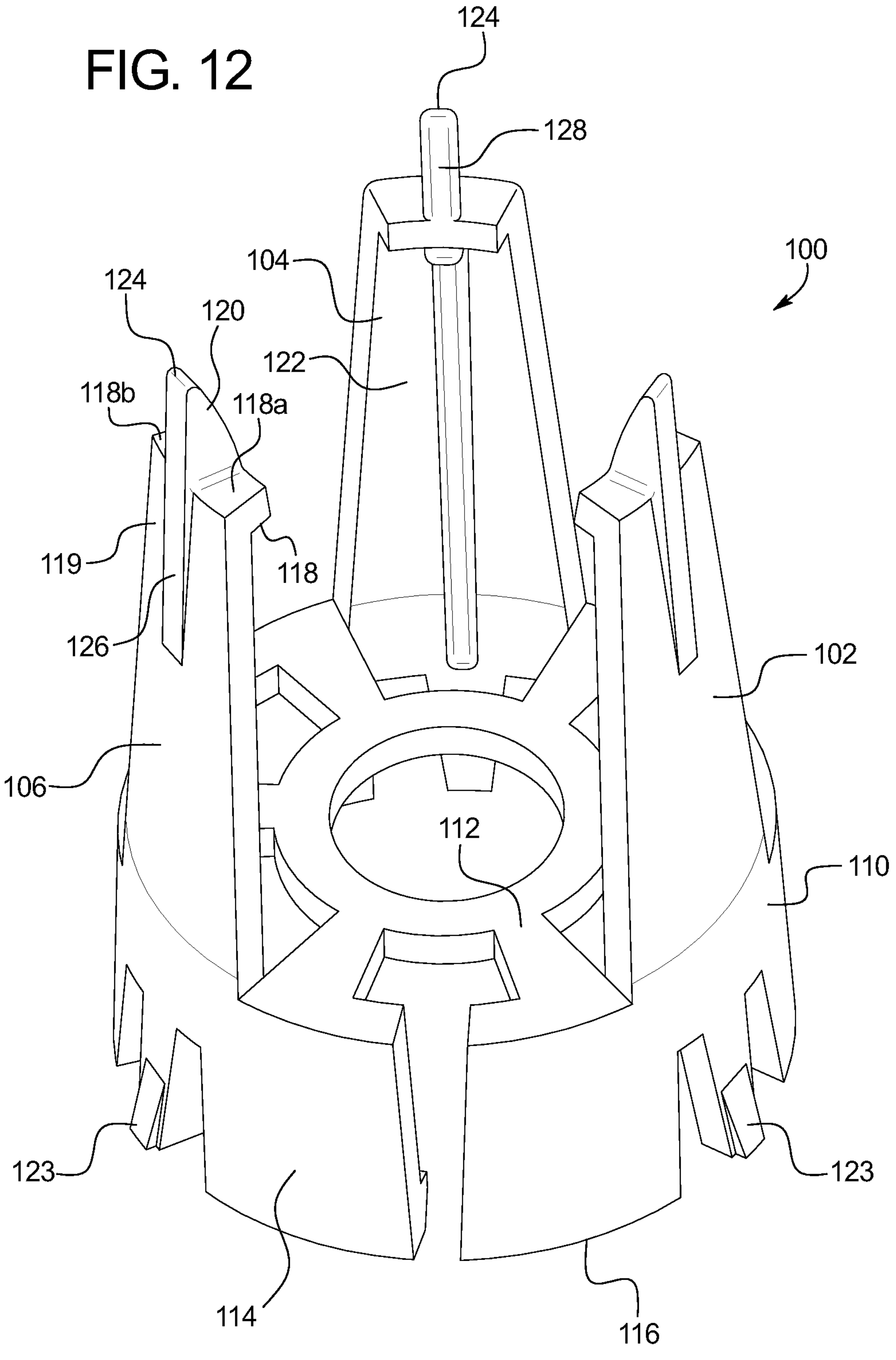
FIG. 12 is a perspective view of one embodiment of the triggering mechanism of the present assembly.

In an unactivated state, the surface of the shoulder 118 resides at least substantially parallel to flange 112 of the circular base 110 of the triggering mechanism 100. Flange 120 includes a base 121, which begins below the surface of shoulder 118 and between shoulder 118*a* and shoulder 118*b*, as shown for example in FIG. 13. Flange base 121 extends from the arcuate inner shoulder wall 122 radially outwardly past the outer shoulder wall 119 of the shoulder 118. An outer edge 126 of tapered flange 120 extends up from outer surface 119 of trigger finger 106 upward to peak 124. An inner surface 128 of flange 120 (as shown in FIG. 12, finger 104) extends from the inner shoulder wall 122, and is tapered radially outward towards peak 124, at which outer edge 126 and inner edge 128 of tapered flange 120 meet.

Figure 13:
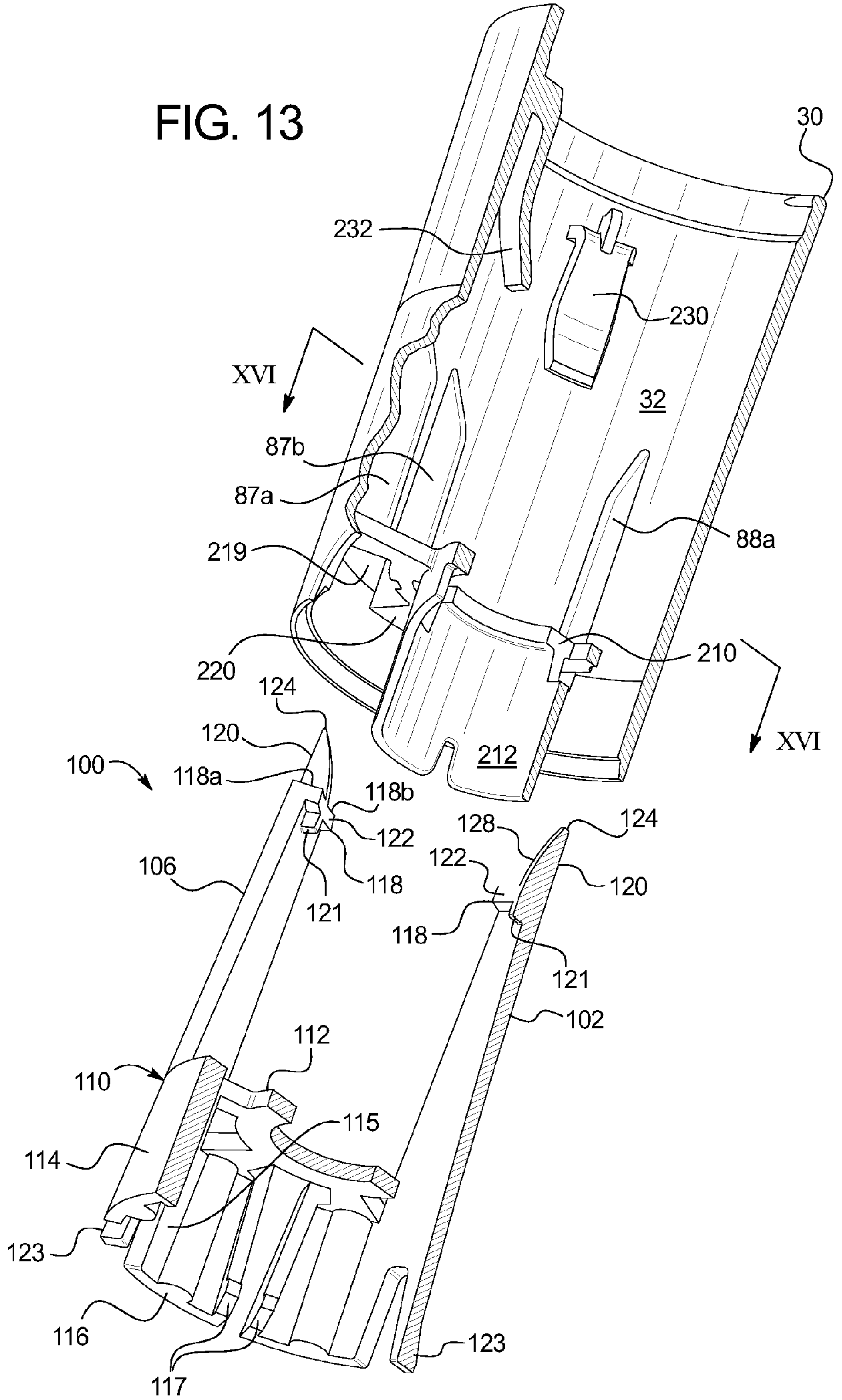
FIG. 13 is an exploded perspective view of one embodiment of the triggering mechanism and a housing sleeve of the reconstitution assembly of the present disclosure in an unengaged configuration.
Figure 14:
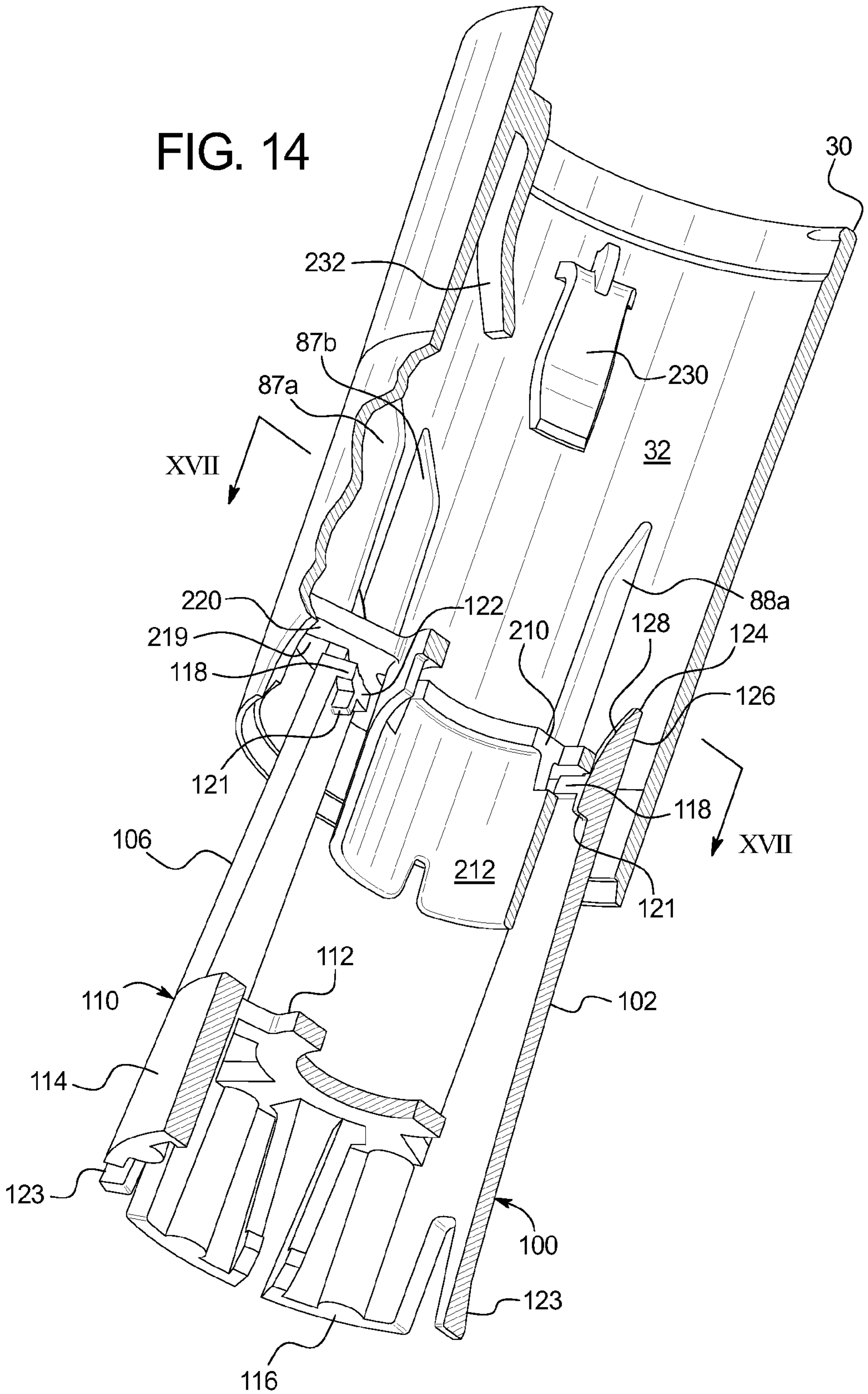
FIG. 14 is an exploded perspective view of the embodiment of the triggering mechanism and a housing sleeve of the reconstitution assembly of FIG. 13 in a partially engaged configuration.
Figure 15:
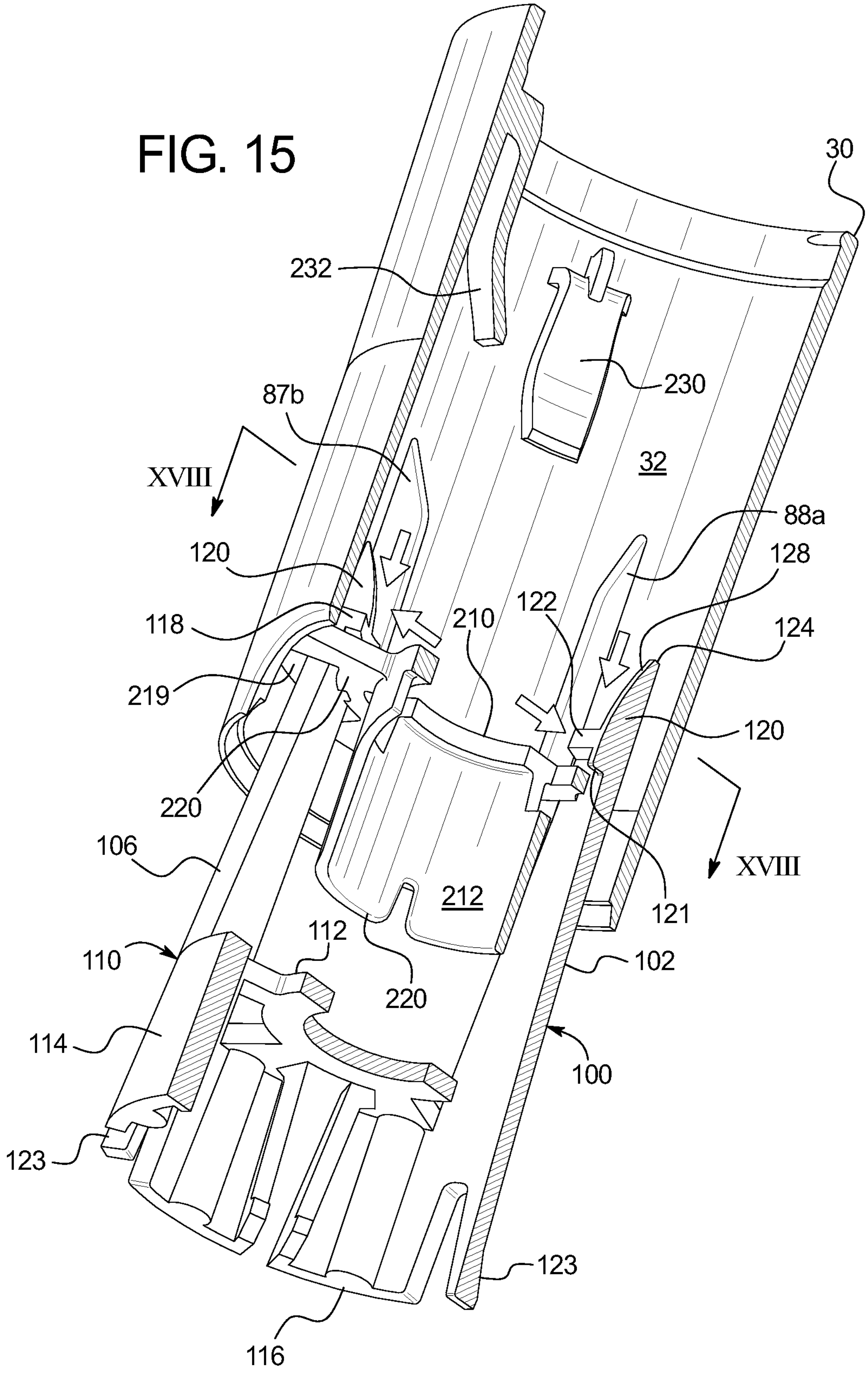
FIG. 15 is an exploded perspective view of one embodiment of the triggering mechanism and a housing sleeve of the reconstitution assembly of FIG. 13 in a fully engaged configuration.

Referring to FIGS. 13 to 15, second sleeve 30 is illustrated in more detail. Second sleeve 30 includes a floor 210 and a generally cylindrical section 212 that is concentric with second sleeve 30 and extends downwardly from the floor 210. Floor 210 of second sleeve 30 includes three radially spaced flanges 220, 222 and 224, which secure the cylindrical section 212 to an inner wall 32 of the second sleeve 30. Only flange 220 is visible in the sectional view of FIGS. 13 to 15, but each of the three flanges 220, 222 and 224 have the same features and geometry in one embodiment. The top views shown in FIGS. 16 to 18, which correspond to the different stages of activation illustrated in FIGS. 13 to 15, respectively, show each of flanges 220, 222 and 224 evenly spaced apart around the upper sleeve 30 at one-hundred twenty degrees.

Second sleeve 30 includes three tab members 230, 232 and 234 attached to inner wall 32 above floor 210 and cylindrical section 212. The three tab members 230, 232 and 234 are likewise spaced evenly about the inner wall 32 of the upper sleeve 30 and are separated by one-hundred twenty degrees. Other numbers and positioning of tabs around the inner wall 31 are also envisioned. The three tab members 230, 232 and 234 (only 230 and 232 are illustrated) are each radially offset from the three flanges 220, 222 and 224 by forty-five degrees and are attached to the inner wall 32 of the second sleeve 30 near its top end, and extend downwardly towards floor 210 and radially inwardly towards the center axis of second sleeve 30.

Referring now generally to FIGS. 3 to 5 and again in FIGS. 6 to 11, the process of activating the reconstitution assembly 10 via triggering mechanism 100 is described in further detail. As mentioned above, reconstitution assembly 10 in one embodiment is packaged so that a sterile environment is maintained about the reconstitution assembly 10. Removal from the package subjects the assembly to the outside environment, except for fluid passageways within the transfer set and the interiors of the vials, which remain sterile and closed to the outside environment.

Prior to activation, and during shipping, first container 70 is held statically in place in first sleeve 30 via tab members 230, 232 and 234 and by washer 72. As discussed above, tab members 230, 232 and 234 are attached to the inner wall 32 of second sleeve 30, and flare downward towards floor 210 of first sleeve 30.

Upon application of a radially outwardly applied force, the tabs flex slightly radially outwardly. First container 70 includes a neck portion 77, which extends from a main body 73 of the first container 70 to a shoulder 74 of the first container. Shoulder 74 includes a rim 75, which defines an opening into which the first seal cap 76 is secured. During assembly when the first container is inserted into the second sleeve 30, rim 75 first contacts tab members 230, 232 and 234 and flex the lower ends of the tabs outwardly to allow the rim 75 to pass over the tabs. The flexing causes the tab members 230, 232 and 234 to be biased radially inward. After the rim 75 has cleared the tab members 230, 232 and 234, the smaller diameter neck portion 77 provides the space to allow the lower portion of the tab members 230, 232 and 234 to spring radially inward towards neck 77. Upon springing radially inward, the unique inward sloping configuration of the tab engages the sloping surface of the container to collectively resist the further downward movement of first container 70. In addition the lower free edge of the tab members 230, 232 and 234 become wedged in between neck 77 and the rim 75 thereby locking first container 70 from upward movement and removal of the container 70 from the sleeve 30 and passageway 11.

First container 70 is now suspended within the sleeve 30 in the resting or unactivated position and pinned by each of the three tab members 230, 232 and 234, such that container 70 is not allowed to shift in the vertical or axial direction absent an applied deliberate downward force.

As shipped, the triggering mechanism 100 of assembly 10 is engaged with lower floor 210 of second sleeve 30. The circular base 110 of triggering mechanism 100 surrounds rim 85 of second container 80. The second container 80 is held against downward movement relative to the trigger mechanism 100 by a series of tabs 115, 117 forming a portion of the upper sleeve as shown in FIG. 13, and shown with second container 80 in FIG. 10 that extend into the space between the rim 111 and neck of the second container. The shape of the tabs 115, 117 engages the underside of the rim 111. The top surface of the second container 80 rests against the flange 112. Thus the flange 112 and tabs 115, 117 bracket and engage the rim 111 of second container 80 and prevent significant relative movement between the container and the triggering mechanism 110. As shown specifically in FIG. 10, the tabs 115, 117 have engaged the underside of the rim 111 of the second container 80, thereby inhibiting lateral movement of the second container 80 in the downward direction. Because triggering mechanism 100 is engaged with the second sleeve 30 to prevent movement prior to activation of the reconstitution assembly 10, second container 80, as braced by triggering mechanism 100, is prevented from shifting relative to the housing 12 prior to activation. The assembly of the trigger mechanism 100 and second container 80 is maintained in a concentric position relative to first sleeve 20, and is limited to vertical or axial displacement by contact between wall section 114 and inner surface of first sleeve 20.

Three pairs of tapered fins, **87*a* and 87*b*, 88*a* and 88*b*, and 89*a* and 89*b* are integrated into second sleeve 30 and spaced radially one-hundred twenty degrees apart. During activation, each of the three trigger fingers 102, 104 and 106 of the trigger mechanism 100 fit in between one of the three pairs of tapered fins, 88*a* and 88*b*, 89*a* and 89*b*, and 87*a*, 87*b* respectively. It should be appreciated that in FIGS. 13 to 15, each of the three pairs of tapered fins 87*a*/87*b*, 88*a*/88*b* and 89*a*/89*b* are not visible in the same view. However, in FIGS. 16 to 18, these tapered fin pairs are visible, and serve to guide each of the fingers 102, 104 and 106 of the trigger mechanism 100 as it moves with respect to the second sleeve 30**, as will be further discussed below.

Figure 16:
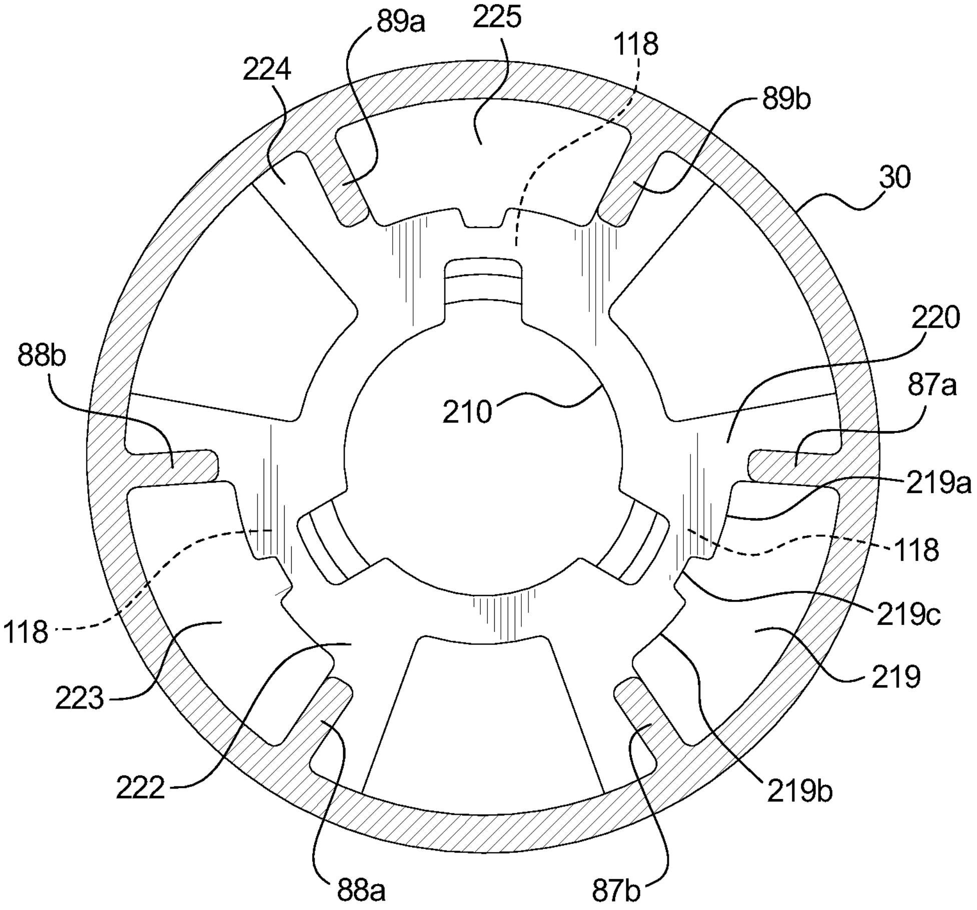
FIG. 16 is a top plan view of FIG. 13 taken along section line XVI-XVI of FIG. 13.

As discussed above, triggering mechanism 100 braces and prevents second container 80 from shifting relative to the housing 12 and subsequently making accidental or premature contact with the lower spike 62 of the lower spike housing of transfer set assembly 40. As assembled within the housing, trigger fingers 102, 104 and 106 of triggering mechanism 100 surround transfer set assembly 40 and extend upwardly and into floor 210 of upper sleeve 30. Each of the three flanges 220, 222 and 224 of floor 210 define an opening 219, 223 and 225, respectively, as seen in FIG. 16, each opening configured to accept the top portion of each of the three trigger fingers 102, 104 and 106. Each of the three openings 219, 223 and 225 in floor 210 of FIG. 16 are identical. It should be appreciated therefore that the discussion of opening 219 corresponding to flange 220 applies equally to openings 223 and 225. The opening 219 is defined by shoulders **219*a* and 219*b* and a notch 219*c*, situated between shoulders 219*a* and 219*b***.

The trigger fingers 102, 104 and 106 as seen in FIGS. 13 to 15 are each angled radially inwardly in the unactivated position. As such, shoulders **118*a* and 118*b*, and inner wall 122 extend toward the center axis of second sleeve 30, and are consequently placed in direct contact with the lower face of flange 220, and specifically the lower surface of shoulders 219*a* and 219*b*. As illustrated in FIG. 14, opening 219 is shaped to accept the upper portion of trigger finger 106. Specifically, as trigger finger 106 travels through floor 210, tapered flange 120 slides into notch 219*c*, and shoulders 118*a* and 118*b* come into contact with the lower portion of shoulders 219*a* and 219*b*. The contact of the shoulders 118*a*, 118*b* with the lower face of shoulders 219*a* and 219*b* of flange 220 prevents the trigger finger 106 from fully traveling through the opening in flange 220, and thus keeps the triggering mechanism 100 static relative to the housing 12. Trigger fingers 102 and 104 are also braced between the corresponding shoulders and the lower face of openings 223 and 225 of the floor 210. Each of the trigger fingers 102, 104 and 106 are positioned below an opening in a different one of the three flanges 220, 224 and 226. The shoulders 118 of each of trigger finger 102, 104 and 106 are braced against the lower face of the floor 210**.

Referring now generally to FIGS. 3 to 5 and 12 to 15, a feature of the triggering mechanism is discussed an illustrated. In various embodiments, the assembly of the triggering mechanism 100, the first container 70 and the lower container 80 into the lower sleeve 20 and upper sleeve 30 is completed prior to shipping to the end user. It should be appreciated that it is undesirable for the user to be able to remove the triggering mechanism 100 and second container from within the lower sleeve and passageway 11. As seen in FIG. 3 and discussed above, during assembly the triggering mechanism 100 and second container 80 are inserted into the lower sleeve 20 from the opening defined by rim 21. In various embodiments, features of the triggering mechanism interact with features of the lower sleeve to prevent disassembly by the user.

As seen in FIG. 12, tabs 123 are integrated onto the wall portion 114 of circular base 110 of the triggering mechanism 100. In the illustrated embodiment, tab 123 is disposed every 120 degrees radially around the circular base 110. It should be appreciated that in various embodiments, greater or fewer numbers and arrangements of tabs 123 can be integrated into the triggering mechanism 100. In various embodiments, tabs 123 are security tabs that interface with the housing 20 to prevent the removal of the triggering mechanism 100 after it is inserted into the lower sleeve 20. The tabs 123 interact with shoulder features 101 defined by the interior wall of the lower sleeve 20 when the triggering mechanism 100 is first inserted into the lower sleeve 20 prior to shipping.

As can be seen more clearly in FIGS. 4 and 5, lower sleeve 20 includes shoulder 101 on its interior wall. It should be appreciated that in various embodiments, shoulder 101 is defined at various predetermined points around the lower sleeve 20, or continuously around the lower sleeve 20. From the bottom of lower sleeve 20 leading up to shoulder 101, the inner wall of lower sleeve 20 starts at a first diameter, and gradually decreases in diameter moving from the bottom of lower sleeve 20 toward the top of lower sleeve 20. In one embodiment, when the inner wall of lower sleeve 20 reaches the shoulder 101, the diameter is at its narrowest. Above the shoulder 101, the inner wall of lower sleeve 20 returns abruptly to its original diameter, which is larger than the diameter defined by shoulder 101. It should be appreciated that, in the embodiment in which the shoulder 101 is not continuously defined all 360 degrees around the inner wall of the lower sleeve 20, the diameter discussed herein refers to the diameter defined by each of the plurality of shoulders 101 around the inner wall of the lower sleeve 20. In one embodiment, the lower sleeve 20 includes three shoulder 101 spaced radially 120 degrees apart.

As seen in FIG. 3 and FIG. 12, the triggering mechanism 100 and second container 80 have just been inserted into the lower sleeve 20. As the triggering mechanism 100, and specifically tabs 123, pass along the narrowing diameter inner wall 20*a* of the lower sleeve 20, the tabs 123 flex inwardly to adjust for the decreasing diameter 20*a* of the lower sleeve 20. As seen in FIG. 12, in one embodiment tabs 123 are disposed on a tab that is separated from the lower portion 110 to enable flexing of the tabs without requiring excess force from the assembler or risk of breaking the triggering mechanism 100. After the tabs 123 have been flexed inwardly to compensate for the decreasing diameter 20*a*, the triggering mechanism 100 continues to move further upward with respect to lower sleeve 20 until it passes shoulder 101. When the tabs 123 pass shoulder 101, the previously inwardly-flexed tabs 123 will flex radially outwardly due to the dramatic increase of diameter defined by shoulder 101. As seen in FIG. 3, the tabs 123 of the triggering mechanism 100 have just been allowed to flex back radially outwardly after having passed shoulder 101. At this stage, if a user were to try and pull the triggering mechanism 100, or the second container 80 connected thereto, back in a reverse direction out of the lower sleeve 20 and passageway 11, the shoulder 101 would prevent any further translation. Thus the trigger mechanism 100 places the second container 80 in the resting or unactivated position by the engagement between the fingers 102, 104, 106 and flange 220 and the engagement between tabs 123 and shoulder 101.

Figure 9:
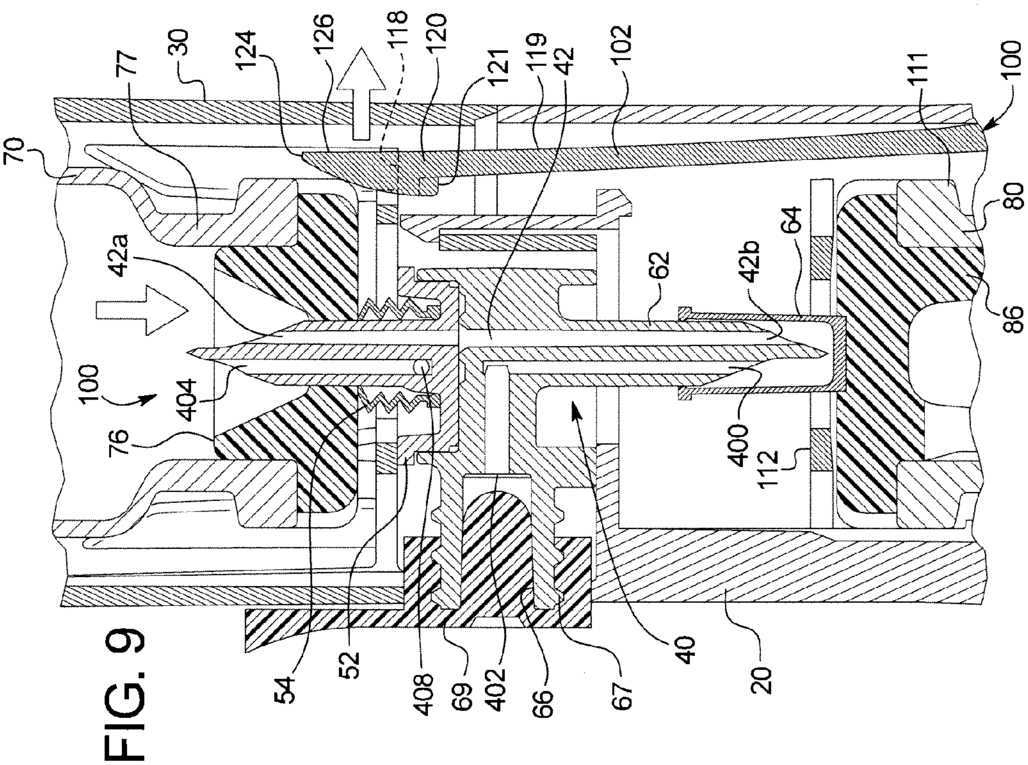
FIG. 9 is a schematic view of the triggering mechanism of FIG. 1 showing a second stage in the use of the reconstitution assembly.
Figure 10:
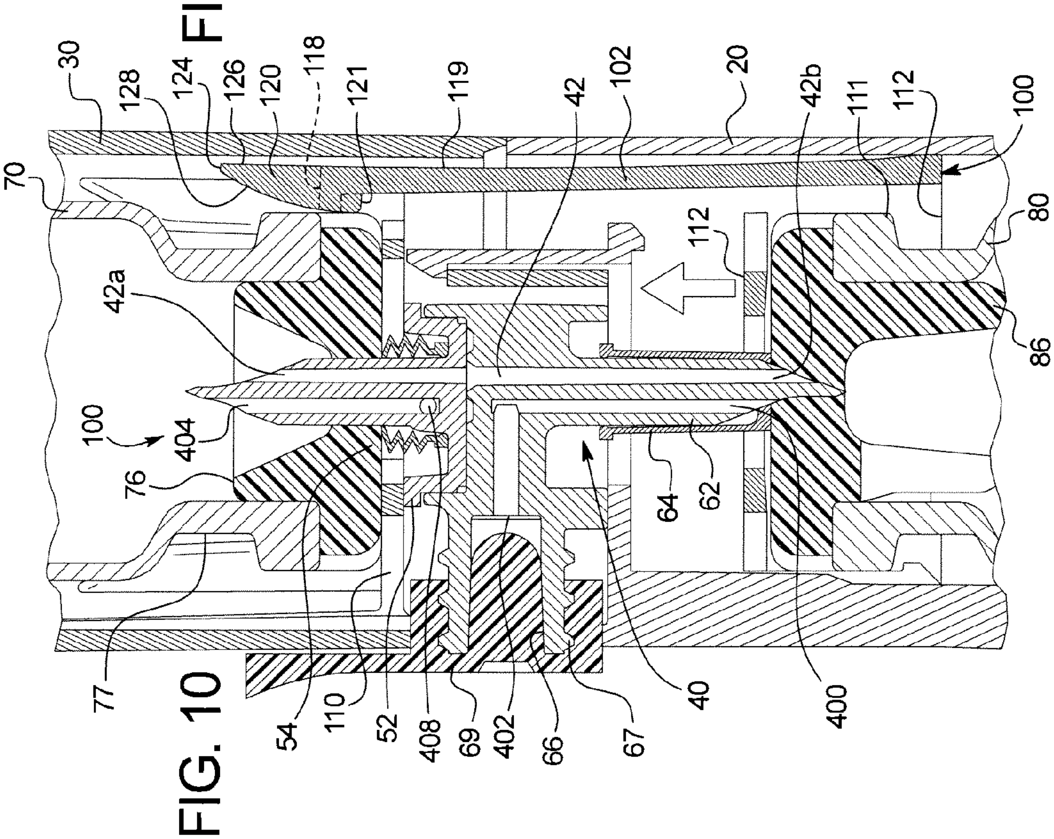
FIG. 10 is a schematic view of the triggering mechanism of FIG. 1 showing a third stage in the use of the reconstitution assembly.

As illustrated in FIG. 4 and again in FIGS. 9, 10 and 14, the patient or caregiver begins the reconstitution process by using one hand to grip the housing 12 and place the reconstitution assembly 10 in a vertical orientation with the lower surface of the second container 80 resting against a surface such as a table or desk. The user will use the other hand and apply a first force downward directly onto the top surface 71 of the first container 70. As the first force is applied to the top portion of the first container 70, the main body 73 makes contact with each of the tab members 230, 232, 234, exerting a force directed radially outward. This contact and force causes the tab members 230, 232, 234 to flex toward the inner wall 32 of second sleeve 30, thereby allowing the main body 73 of the first container 70 to become freed from the suspension force within second sleeve 30. As tab members 230, 232 and 234 are flexed out of the path of the main body 73, first container 70 is free to begin traveling axially downward in a vertical direction toward the transfer set assembly 40. The tab members 230, 232, 234 arranged at one-hundred twenty degree radial increments around the first container 70 and gasket 72 keeps the first container centered and concentric to first sleeve 30.

FIGS. 4, 9 and 10 show that as first container 70 is forced past the three tab members 230, 232 and 234, first seal cap 76 crumples or compresses upper boot 54 of the transfer set assembly 40. As the force from the first container increases, and the transfer set assembly 40 resists that force, the upper spike end of the upper spike 52 pierces through the upper boot 54. Once through the upper boot 54, the upper spike end of the upper spike 52 pierces the seal cap 76 of the first container 70. As, first container 70 is moved further axially downwardly, the upper spike end of the upper spike 52 fully penetrates first sealing flange 76, such that the fluid contents 73 of the first container 70 are placed in fluid communication with the transfer set assembly 40 through upper end 42*a* of the flow path 42 and the upper spike 52.

Figure 17:
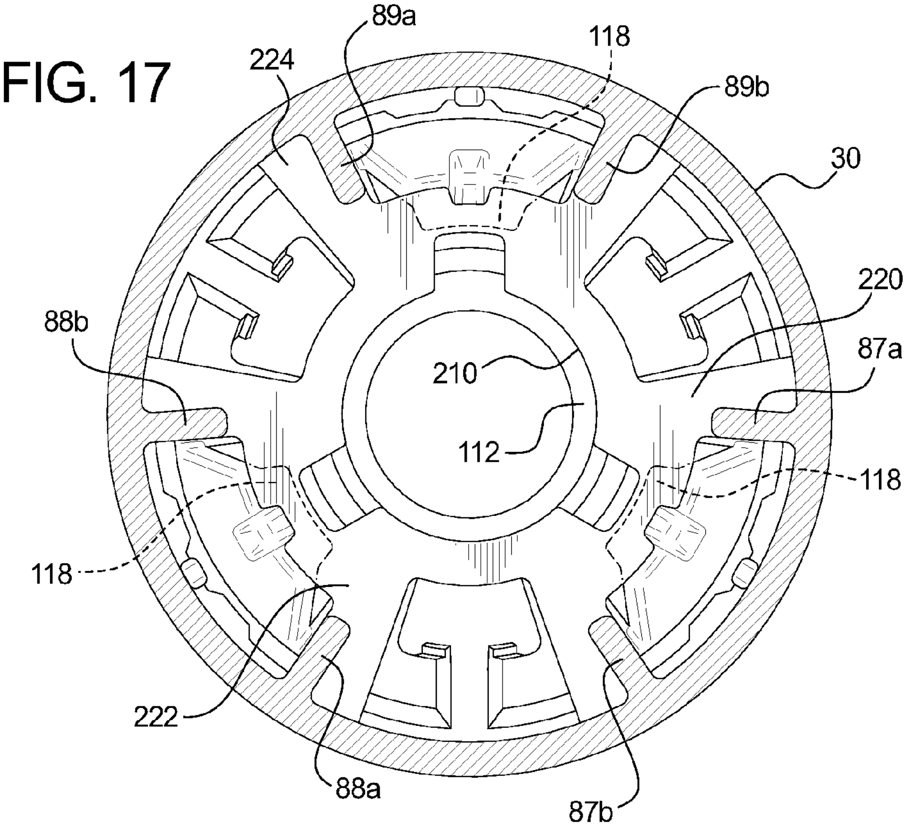
FIG. 17 is a top view of FIG. 14 taken along section line XVII-XVII of FIG. 14.

After the upper spike end of the upper spike 52 has fully penetrated the seal cap 76 of the first container 70, the first container 70 is enabled to continue to move axially downward towards transfer set assembly 40. The continued downward force and movement of the first container 70 following the penetration of the seal cap 76 starts the activation of the triggering mechanism 100. As described above, in the unactivated position, the shoulders 118*a* and 118*b* of the trigger fingers 102, 104 and 106 of the triggering mechanism 100 are braced against the lower face of the flange 220, and the tapered flange 120 of trigger fingers 102, 104 and 106 extend through opening in the floor 210. When first container 70 is forced axially downwardly, rim 75 of seal cap 76 contacts the inner surfaces 128 of the tapered flanges 120 on trigger fingers 102 to 106, which are protruding through the floor 210 of the second sleeve 30 as seen at FIGS. 9, 14 and 17. Simultaneously, the rim 75 also contacts the corresponding tapered flanges on each of the other two trigger fingers 102, 104 around the circumference of the first container 70. In an embodiment, the first seal cap 76 may be formed such that the outer radial exterior surface may extend outward such that the first seal cap may initially contact the trigger fingers 102, 104, 106.

Due to the tapered profile of the flange 120, the further the first container moves axially downward relative to second sleeve 30, the more force will be exerted in a radially outward direction against the top of each of the three trigger fingers 102, 104 and 106. The resultant radially outward force applied on the tapered flange 120 by the downward shifting first container 70 causes each of the trigger fingers 102, 104, 106 to flex in a radially outward direction as seen in FIGS. 9 and 10.

As a result of the trigger fingers 102, 104, 106 each being simultaneously flexed outward and toward the inner wall 32 of second sleeve 30, the shoulder 118 moves away from the lower surface of the floor 210. Once the shoulder 118 is forced radially outward, the shoulders 118*a* and 118*b* lose contact with the lower surface, and shift into the opening in the floor 210. As described above, prior to engagement of the rim 75 and tapered flanges 120, the triggering mechanism 100 is braced from movement relative to the first sleeve 30 by contact between the shoulders 118*a*, 118*b*, and shoulders 219*a* and 219*b* of the lower surface of the floor 220. Because shoulders 118 have now been disengaged from this braced position, the triggering mechanism 100 is now free to shift axially relative to the housing 12. It should be appreciated that the rim 75 is not configured to activate the triggering mechanism 100 or make contact with any of the tapered flanges 120 of the trigger fingers 102, 104, 106 until after the upper spike end of the upper spike 52 has penetrated the first seal 76 and put the flow path 42 of the transfer set assembly 40 into fluid communication with the fluid contents of the first container 70.

As downward force is continually applied on the first container 70, the container continues to move axially downward toward the transfer set assembly 40 until the rim 75 contacts the floor 210 of the upper sleeve 30. At the point when the rim 75 of the first container 70 sits flush against the top surface of floor 210, each of the three trigger fingers 102, 104, 106 have been flexed radially outward, as discussed above, and the first container 70 is prevented from shifting any further relative to the housing 12. It should be appreciated that, at this point in the reconstitution process, the transfer set assembly 40 and the first container 70 are in fluid connection with one another. Lower boot 64 maintains fluid within the first container 70 and the transfer set assembly 40 as seen in FIGS. 4 and 8.

Figure 11:
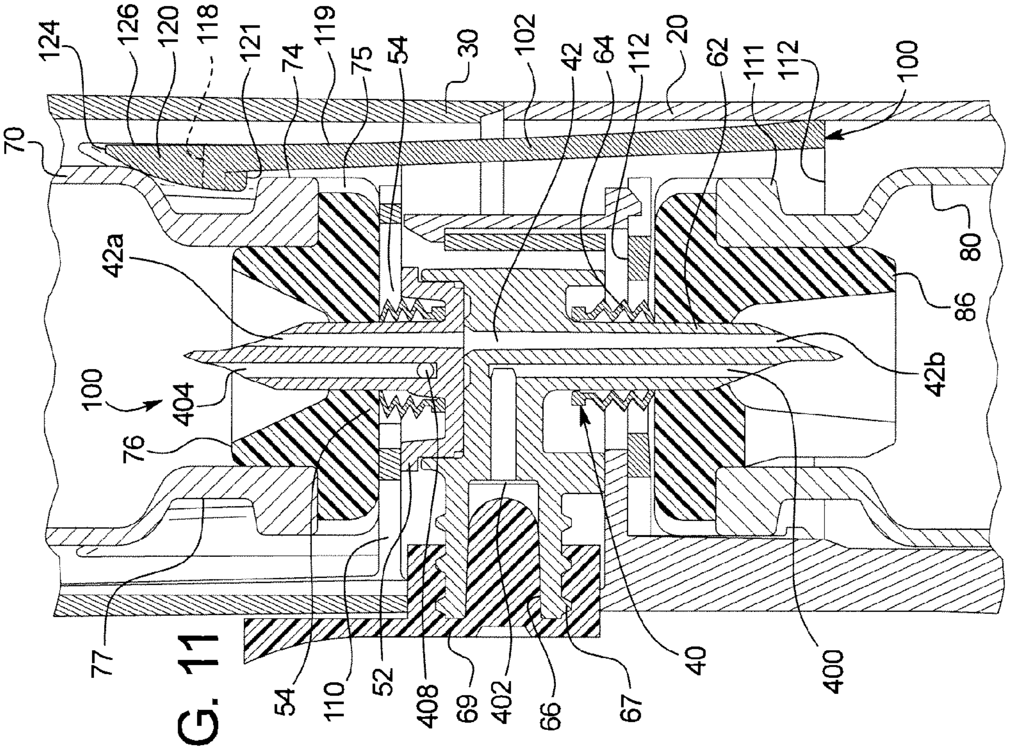
FIG. 11 is a schematic view of the triggering mechanism of FIG. 1 showing a final stage in the use of the reconstitution assembly.
Figure 18:
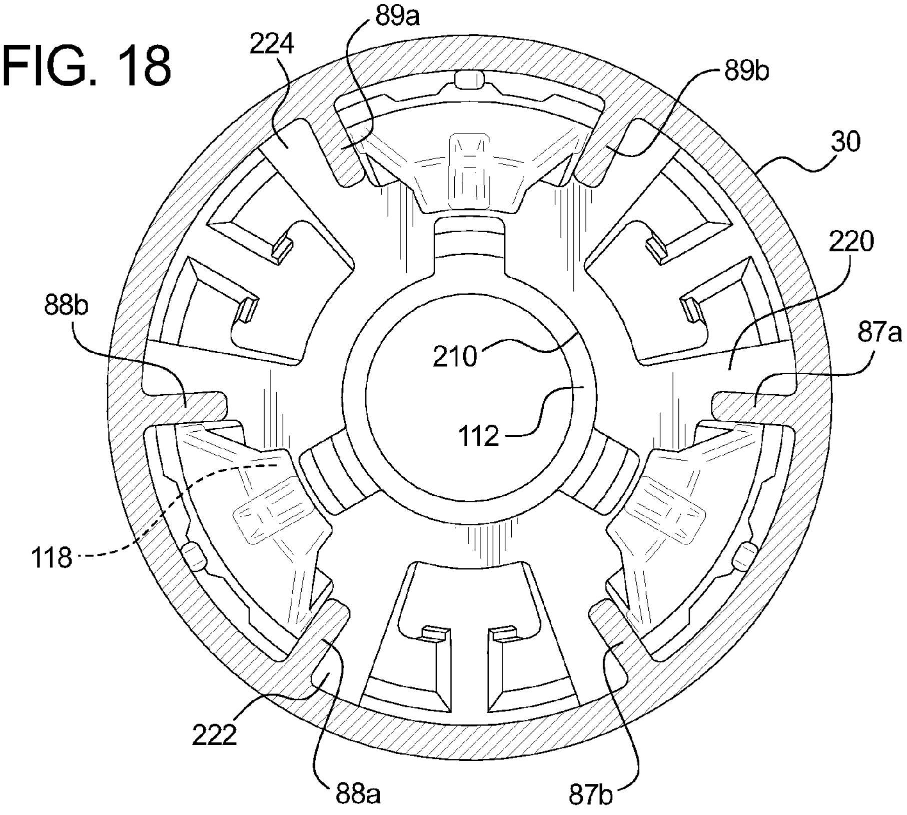
FIG. 18 is a top view of FIG. 15 taken along section line XVIII-XVIII of FIG. 15.

Referring to FIGS. 10 and 11, the second container 80 is no longer prevented by the triggering mechanism 100 from movement relative to the floor 210 of second sleeve 30, because the trigger fingers 102, 104 and 106 have been freed from engagement and now the mechanism is allowed to shift relative to the housing 12, sliding along rim 75 and bottlehead 74. As shown in FIGS. 10, 15 and 18, continued force on the top 71 of the first container 70 results in movement of the entire housing 12, first container 70, and transfer set assembly 40 downwardly relative to and toward the second container 80.

As the housing 12, first container 70, and transfer set assembly 40 move together axially downward relative to the second container and the trigger mechanism 100, the transfer set assembly 40 comes into contact with the second seal cap 86 of the second container. More specifically, first the lower boot 64 contacts the second seal cap 86 of the second container 80. As the force of the downwardly shifting transfer set assembly 40 increases against the second seal cap 86 of the second container 80, the resistance of the lower boot 64 and the second seal cap 86 give way to the lower tip of the lower spike 62. The lower tip of the lower spike 62 pierces the lower boot 64, and then continue to pierce the second seal cap 86 to put interior of the second container 80 in fluid communication with the lower end 42*b* of the flow path 42 and thereby in fluid communication with the interior of first container 70 via the flow path 42 of the transfer set 40 as seen in FIGS. 5 and 9.

It should be appreciated that in one embodiment, as the housing 12, first container 70 and the transfer set assembly move downward relative to the second container 80 and the triggering assembly 100, the trigger fingers 102, 104 and 106 will naturally move radially inwardly back to their natural inward biased configuration after the rim 75 of the first container 70 has passed the tapered flange 120 of each trigger finger. The tapered flange 120 will then move into the volume around the neck 77 of the container. The lower surface 121 will then wedge against the upper surface of the shoulder 74 to prevent relative separation movement of the container 70 and the container 80. The first container 70 and second container 80 are thereby clamped together and to the transfer assembly by the trigger assembly 100 thereby retaining the containers within the passageway 11 and housing 12.

As seen in FIGS. 3 to 5, in various embodiments, the first container 70 includes a locking or resistance feature that interfaces with a gasket 72 of housing 12 to prevent relative separation movement of the container 70 and the container 80. It should be appreciated that the locking feature could be integrated into the first container 70 at the time of manufacture, or could be added to the first container 70 before assembly. In the illustrated example embodiment, the product label 79 is used as the locking feature on container 70. In this embodiment, the gasket 72 is toleranced so that the gasket 72 stretches over the product label 79 on the first container 70. Because it is stretched, the gasket 72 is biased radially inward when sliding along the portion of the first container 70 with the product label 79. In various embodiments, the gasket 72 is constructed out of a plastic or polymeric material.

It should be appreciated that in various embodiments, the product labels 79, 89 are made of a plastic film which is more impervious to hydrogen peroxide and other sterilization chemicals than paper labels. Additionally, it should be appreciated that the plastic labels afford better friction for the labels 79, 89 to pass easily through the gaskets 72, 82 respectively. In various embodiments, the product labels 79, 89 do not wrap completely around the first and second containers 70, 80, and the label does not overlap upon itself in any location. In one embodiment, the label covers about 350 degrees of the respective container. It should be appreciated that any overlap of the label could unduly increase the force required to activate the assembly.

In reference to FIG. 5, as discussed above, upon delivery of the reconstitution assembly, the first container 70 and second container 80 are already assembled in the housing 12. Once the first container 70 and the second container 80 are placed in fluid communication with one another via the transfer set assembly 40, it is desirable to prevent separation of the two containers 70, 80. In operation, the first container 70 is pushed downward with respect to the second container 80. As the first container 70 is moving downward within the housing 12 toward the second container 80, the gasket 72 disposed on the housing 12 surrounds and contacts the product label 79 on the first container 70. In one exemplary embodiment, the product label 79 has a specifically designated thickness, and is affixed to the first container 70 at a first specific location. When the gasket 72 has fully passed the product label 79, and specifically the edge 79*a* of the product label 79, as the first container 70 travels downward, the gasket 72 passes the edge 79*a* of the product label 79, and the gasket's 72 radially inward bias will cause it to contract around the outer surface of the first container 70. Due to the tolerancing of the gasket 72 and the thickness of the product label 79, this mechanism operates to prevent a user from shifting the first container in an opposite direction, thereby preventing undesirable separation of the first and second containers. If a user would attempt to shift the first container in the opposite direction, the lower edge 72*a* of the gasket 72 abuts the edge 79*a* of the product label 79, thereby preventing further translation of the container relative to the housing. It should be appreciated that second container 80 also includes a similarly dimensioned product label 89 and gasket 82. The gasket 82, gasket edge 82*a*, product label 89 and product label edge 89*a* operate in the same fashion to prevent separation of the second container from the lower sleeve 20.

As seen in FIG. 5, once the gaskets 72 and 82 each clear the entire product label 79 and 89 respectively, reversing direction and stretching back over the product label, allowing withdrawal of the first container 70, would require overcoming the resistance of the gaskets 72, 82, and specifically the gaskets' edges 72*a*, 82*a* abutting the edges 79*a*, 89*a* of the product labels 79, 89 of containers 70 and 80 respectively.

It should be appreciated that, in various embodiments, different sized containers are usable with the same housing 12. For example, in various embodiments, the first container 70 and second container 80 are swapped out for a larger first container and a larger second container, which correspond with a different drug, reconstitution or treatment. One would appreciate that using the same housing for multiple different types of drugs and treatments provides valuable flexibility and versatility. It should be appreciated that, regardless of the diameter dimensions of the containers being used, the neck of all containers is standardized according to ISO or another standardization convention, and is predictable in the industry. Therefore, when a larger-sized container is swapped with the container 70 or 80 discussed above, the trigger fingers, locking mechanism and transfer set assembly will all still interface consistently. In various such embodiments, the only parts that need be modified are the gaskets 72, 82 and the ribs 87*a*, 88*a*, 89*a* used to center the container. It should be appreciated that in various embodiments, the upper sleeve 30 and lower sleeve 20 includes a plurality of ribs, similar to ribs 87*a*, 87*b* and 87*c* in a first position and a plurality of ribs in a second position, depending upon the diameter of the containers being used. In various embodiments, it should be appreciated that the modified gaskets replacing gaskets 72, 82 when swapped out for a larger-diameter container, are color coordinated to easily notify the user which type of drug or container is to be used.

As discussed above, the contents of the second container 80 are vacuum-sealed. Therefore, when the lower end 42*b* of the flow path 42 is placed in fluid communication with the interior of the second container, the sealed vacuum is exposed to the flow path 42. The negative pressure level inside the second container is then equalized by pulling fluid 73 from the first container 70 through the flow path 42 facilitated by the transfer set 40 into the second container 80. When the fluid 73 has been fully transferred from the first container 70 through the transfer set assembly 40 and into the second container 80, the solid contents 83 of the second container 80 are mixed with the liquid contents 73 from the first container 70 to form a reconstituted drug. In one embodiment, the patient or caregiver gently agitates the entire reconstitution assembly 10 to mix the liquid contents 73 and the solid contents 83 adequately to form a homogeneous mixture for use as an, e.g., injectable drug. It should be appreciated that due to the penetration of the upper spike and lower spike into the interior of the first container and lower container the fluid path after activation has completed is limited to the first container 70, the transfer set assembly 40, and the second container 80. Post-agitation, the reconstituted drug will not escape this sealed boundary.

Referring now to FIGS. 6 and 7, a more detailed view of the transfer set 40 is illustrated. FIG. 6 illustrates a cutaway view of the transfer set 40 having a port 66, lower flow path end 42*b* and upper flow path end 42*a*. Transfer set 40 defines a venting path 404 in the upper spike housing 52, and an access pathway 400 fitted with a filter 402 or valve in the lower spike housing. It should be appreciated that in various embodiments, filter 402 or valve is a check valve.

FIG. 7 illustrates the transfer set 40 of FIG. 6 as sectioned along line VII-VII of FIG. 6. It should be appreciated that when the fluid is being transferred from the first container 70 to the second container 80 to prevent a vacuum from being pulled in the sealed second container, air must replace the transferred fluid. Venting path 404 is connected to vent port 406, which accesses the ambient air outside of the sealed transfer set 40. Vent port 406 includes a hydrophobic filter 408 to allow filtered air to enter from outside of the transfer set 40 into vent port 406, through the venting path 404, and into the first container 70. Filter 408 is hydrophobic in one embodiment, so any fluid which travels down venting path 404 and into port 406 cannot leak outside of the transfer set assembly 40 through filter 408 or be contaminated. Filter 408 is selected to prevent pathogens in the air from entering the insides of containers 70 and 80. The porosity of the filters can vary anywhere from about 0.2 microns to 150 microns. In various embodiments, the venting port filter 408 is both hydrophobic as discussed above, and also oleophobic, which prevents any leakage onto the filter of silicone or other lubricious lubricant used on the spike tip from clogging or blocking of the vent pores.

After the drug has been fully reconstituted, the patient or caregiver accesses the reconstituted drug through the withdrawal port 66 of the lower spike housing of the transfer set assembly 40. To facilitate complete emptying of the second container 80, the user will typically flip the assembly 10 so that the second container is now at the top of the assembly. Withdrawal port 66 is configured as a female luer connector and extends radially outward from the lower spike housing. In an embodiment the port 66 includes a series of threads 67 to provide a sealed connection with a male luer tip having an annular locking flange. Port seal 69 is configured to engage or overwrap threads 69 and sealingly enclose the withdrawal port 66. Disposed inside of withdrawal port 66 is product filter 402 in one embodiment, which is configured to prevent any unmixed solid particulate 83 from the reconstituted drug from being withdrawn.

As seen in FIG. 6, the transfer set 40 includes port 66, which enables a user to remove the reconstituted drug from the reconstitution assembly 10 through access pathway 400 formed in the transfer set assembly 40. As seen in FIG. 4, withdrawal port 66 extends through the housing 12 and is exposed to the exterior of the housing. As discussed with FIG. 11, a portion of the lower spike 62 penetrates seal cap 86 to place flow path 42 and access pathway 400 in fluid communication with the interior of second container 80. In an embodiment access pathway 400 may include a check valve (not illustrated), which can be opened by inserting a syringe or male luer into the port 66. It should be appreciated that the one way check valve (not illustrated) both allows removal of the contents by the user and prevents air from entering into the transfer set assembly 40 from the port 66 if the user mistakenly removes the port seal 69 prior to withdrawal. In alternative reconstitution assembly 10 embodiments, port cap 69 is no longer necessary, because the check valve keeps contaminating air out of the internal sterile environment during activation, but allows for access of the liquid when opened by a luer or syringe end. It should also be appreciated that a check valve acts to prevent an important misuse of the product. In some situations, if the user mistakenly attaches a syringe to the port and instead of pulling the syringe to extract the drug, pushes the syringe, the net result without a check valve would be to force the solution from the second container 80 to the first container 70. A check valve prevents this misuse. Any resulting introduction of air through the extraction port 66 would result in the waste of valuable drugs.

Access pathway 400 provides fluid communication between port 66 and the interior of second container 80 (which contains the reconstituted drug). The user is then enabled to draw the reconstituted drug out of the second container 80 through the access pathway 400, and port 66, and into a medical syringe or other suitable medical apparatus without the use of needles. In an embodiment including a check valve (not illustrated) along the access pathway 400 the fluid will be able to pass through the check valve.

It should be noted that while the user is gripping the housing and applying a force to the first container 70 to cause initial movement of the first container relative to the housing 12 followed by movement of the second container relative to the housing, the external configuration of the housing remains static or fixed. This is important because the gripping force applied by the user is directed radially inward. If the reconstitution process required radially outward flexing or distortion of the housing the gripping force applied by the user may actually interfere with the movement of the containers or other aspects of the reconstitution process.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A reconstitution assembly comprising:

(a) a housing having a generally cylindrical shape;

(b) a first container disposed within the housing and configured to be axially displaced relative to the housing, the first container having a first opening sealed with a first seal cap;

(c) a second container disposed within the housing having a second opening sealed with a second seal cap, wherein the first container is arranged within the housing coincident to the second container;

(d) a transfer set assembly disposed within the housing and between the first container and the second container, the transfer set assembly configured to fluidly access first contents through the first seal cap of the first container and fluidly access second contents through the second seal cap of the second container; and (e) a triggering mechanism configured to ensure that the first contents of the first container are accessed by the transfer set assembly before the second contents of the second container are accessed by the transfer set assembly, the triggering mechanism having a base portion engaged with the second container and a plurality of fingers extending from the base portion, the triggering mechanism operable in an unactivated state and an activated state, wherein:

(i) in the unactivated state, the plurality of radially spaced fingers engage with the housing to prevent axial displacement of the second container relative to the housing and the transfer set assembly; and (ii) in the activated state:

(1) first, the first container is axially displaced relative to the housing and the transfer set assembly so that the transfer set assembly pierces the first seal cap to access the first contents, the first container then causing the trigger fingers to disengage from the housing after the transfer set assembly has accessed the first contents, and (2) second, the second container is axially displaced relative to the housing and the transfer set assembly so that the transfer set assembly pierces the second seal cap to access the second contents.

2. The reconstitution assembly of claim 1, wherein the transfer set assembly includes a first spike end to pierce the first seal cap and a second spike end to pierce the second seal cap.

3. The reconstitution assembly of claim 2, wherein the transfer set assembly includes a first boot covering the first spike end and a second boot covering the second spike end.

4. The reconstitution assembly of claim 3, wherein at least one of the boots is arranged to prevent the first and/or second contents from entering and leaving the respective first or second spike end.

5. The reconstitution assembly of claim 1, wherein the transfer set assembly includes a withdrawal port in fluid communication with at least one of the first container and the second container.

6. The reconstitution assembly of claim 5, wherein the withdrawal port extends through the housing.

7. The reconstitution assembly of claim 2, wherein at least one of the first and second seal caps is constructed and arranged to compressively and sealingly hold the first or second spike end of the flow path once pierced.

8. The reconstitution assembly of claim 1, wherein at least one of (i) the first contents is an injectable quality liquid; (ii) the second contents includes a lyophilized drug; and (iii) the second container holds a vacuum prior to the second seal cap being pierced.

9. The reconstitution assembly of claim 1, wherein the housing includes a first portion abutting a second portion, the first housing portion holding the first container, the second housing portion holding the second container, the trigger fingers of the triggering mechanism engaged with the first housing portion in the unactivated state.

10. The reconstitution assembly of claim 7, the first housing portion defining a plurality of apertures, each aperture sized to receive one of the trigger fingers.

11. The reconstitution assembly of claim 7, wherein the transfer set assembly is held fixed between a first housing portion and a second housing portion.

12. The reconstitution assembly of claim 1, wherein the first container spreads the trigger fingers apart radially to disengage from the housing.

13. The reconstitution assembly of claim 1, wherein the housing holds the first container via at least one flexible tab, the flexible tab configured to flex to allow the first container to be axially displaced towards the transfer set assembly.

14. The reconstitution assembly of claim 1, wherein the first container includes a first product label configured to interface with a first gasket attached to the housing to inhibit an opposite axial displacement of the first container after completion of the activated state.

15. The reconstitution assembly of claim 1, wherein the second container includes a second product label configured to interface with a second gasket attached to the housing to inhibit an opposite axial displacement of the second container after completion of the activated state.

16. The reconstitution assembly of claim 1, wherein following the activated state, the trigger fingers of the triggering mechanism engage with the first container to inhibit axial movement of the first container away from the transfer set assembly.

17. The reconstitution assembly of claim 1, wherein the base portion of the triggering mechanism engages with the second container in the unactivated state to inhibit axial movement of the second container away from the triggering mechanism.

18. A reconstitution assembly for reconstituting a medication contained in a first container with a diluents contained in a second container, the first container including a first opening sealed with a first penetrable seal cap, the second container including a second opening including a second penetrable seal cap, the assembly comprising:

(a) a housing forming a passageway, at least a portion of the first container disposed within the passageway, the housing moveably retaining the first container in a first resting position, at least a portion of the second container disposed in the passageway, the first and second containers arranged such that the first opening of the first container faces the second opening of the second container;

(d) a transfer set assembly attached to the housing and positioned between the first container and the second container, the transfer set assembly including a first spike extending toward the first penetrable seal cap and a second spike extending toward the second penetrable seal cap, the assembly forming a flow path extending through at least a portion of the first spike and a portion of the second spike, the first spike not penetrating the first seal cap when the first container is in the first resting position;

(c) a triggering mechanism configured to engage the second container and including a plurality of fingers extending within the passageway to releasably engage the housing and maintain the second container in a second resting position with the second seal cap not penetrated by the second spike, the fingers configured to be engaged by the first container after the first container moves past a first activated position with at least a portion of the first spike penetrating the first seal cap to establish fluid communication between the interior of the first container and the flow path, the engagement of the first container to the fingers disengaging the fingers from the housing sufficiently to allow the second container to move toward the first container to a second activated position with at least a portion of the second spike penetrating through the second seal cap to establish fluid communication with the flow path.

19. The assembly of claim 18 wherein the transfer assembly forms an access pathway and an exterior portion of the transfer assembly extends through the housing to form a withdrawal port for access by a user, the access pathway providing fluid communication between the withdrawal port and a portion of the second spike.

20. The assembly of claim 19 wherein the access pathway is formed to provide fluid communication between the interior of the second container and the withdrawal port when the second container is in the activated position.

21. The assembly of claim 18 wherein the first container includes a shoulder extending about the opening, the fingers of the triggering mechanism configured to engage the shoulder when the second container is in the second activated position to prevent return movement of the first container to the first resting position.

22. The assembly of claim 18 wherein the housing maintains a static configuration as the first container moves from the first resting position to the first activated position and the second container moves from the second resting position to the second activated position.

23. A method for reconstituting a medication comprising reconstitution assembly comprising:

placing a housing in a first orientation, the housing forming a passageway and at least a portion of a first container disposed within the passageway with an end of the first container extending outward from a first rim of the housing, at least a portion of a second container disposed in the passageway with an end of the second container extending outward from a second rim of the housing, the first and second containers arranged such that a first seal cap sealing an opening of the first container faces a second seal cap sealing an opening of the second container, a transfer set assembly positioned between the first container and the second container, the transfer set assembly including a first spike extending toward a first seal cap and a second spike extending toward a second seal cap, the transfer set assembly forming a flow path extending within the spikes and including a withdrawal port that extends through a side of the housing;

placing the second end of the second container against a surface;

exerting a force against the first end of the first container, the force moving the first container relative to the housing toward the transfer set assembly at least until the first spike penetrates a first seal cap of the first container sufficiently to place the flow path in fluid communication with an interior of the first container, preventing movement of the second container toward the transfer set assembly at least until fluid communication is established between the flow path and the interior of the first container, at least after the fluid communication is established between the flow path and the interior of the first container, the force moving the second container toward the transfer set assembly at least until the second spike pierces a second seal cap of the second container sufficiently to place the flow path and an access pathway formed by the transfer set assembly in fluid communication with the interior of the second container;

flowing a fluid in the first container into the second container through the flow path;

mixing the fluid with medication contained within the second container to form a reconstituted medication; and withdrawing the reconstituted medication through the access pathway and withdrawal port, while portions of the first and second containers remain within the passageway and the first and second seal caps remain pierced by the transfer set assembly.

* * * * *